(12) United States Patent
Jin et al.

US008748140B2

(10) Patent No.: US 8,748,140 B2
(45) Date of Patent: Jun. 10, 2014

(54) XYLOSE-FERMENTING MICROORGANISM

(71) Applicant: The Board of Trustees of the University of Illinois, Urbana, IL (US)

(72) Inventors: Yong-Su Jin, Champaign, IL (US); Soo Rin Kim, Savoy, IL (US); Suk-Jin Ha, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/656,613

(22) Filed: Oct. 19, 2012

(65) Prior Publication Data

US 2013/0102046 A1 Apr. 25, 2013

Related U.S. Application Data

(60) Provisional application No. 61/550,333, filed on Oct. 21, 2011.

(51) Int. Cl.
*C12P 7/06* (2006.01)
*C12N 1/20* (2006.01)
(52) U.S. Cl.
USPC ........................................ 435/161; 435/252.3
(58) Field of Classification Search
USPC .............................................. 435/252.3, 161
See application file for complete search history.

(56) References Cited

U.S. PATENT DOCUMENTS 7,285,403 B2 10/2007 Jeffries et al.
2001/0010913 A1 8/2001 Hillman et al.

FOREIGN PATENT DOCUMENTS

WO 2011/123715 A1 10/2011

OTHER PUBLICATIONS

Altschul et al., "Basic Local Alignment Search Tool", J. Mol. Biol., vol. 215, 1990, pp. 403-410.
Altschul et al., "Gapped BLAST and PSI-BLAST: A New Generation of Protein Database Search Programs", Nucleic Acids Research, vol. 25, No. 17, 1997, pp. 3389-3402.
Argueso et al., "Genome Structure of a *Saccharomyces cerevisiae* Strain Widely used in Bioethanol Production", Genome Research., vol. 19, Oct. 7, 2009, pp. 2258-2270.
Batt et al., "Direct Evidence for a Xylose Metabolic Pathway in *Saccharomyces cerevisiae*", Biotechnology and Bioengineering, vol. XXVIII, 1986, pp. 549-553.
Corpet, Florence, "Multiple Sequence Alignment with Hierarchical Clustering", Nucleic Acids Research, vol. 16, No. 22, 1988, pp. 10881-10890.
Eisen, Jonathan A., "Phylogenomics: Improving Functional Predictions for Uncharacterized Genes by Evolutionary? Analysis", Genome Research, vol. 8, 1998, pp. 163-167.
Feng et al., "Progressive Sequence Alignment as a Prerequisite to Correct Phylogenetic Trees", Journal of Molecular Evolution, vol. 25, 1987, pp. 351-360.
Karlin et al., "Applications and Statistics for Multiple High-Scoring Segments in Molecular Sequences", Proc., Natl. Acad. Sci. USA, vol. 90, Jun. 1993, pp. 5873-5877.
Karlin et al., "Methods for Assessing the Statistical Significance of Molecular Sequence Features by Using General Scoring Schemes", Proceedings of the National Academy of Sciences of the United States of America, vol. 87, No. 6, Mar. 1990, pp. 2264-2268.
Needleman et al., "A General Method Applicable to the Search for Similarities in the Amino Acid Sequence of Two Proteins", J. Mol. Biol.,vol. 48, 1970, pp. 443-453.
Pearson et al., "Improved Tools for Biological Sequence Comparison", Proc. Natl. Acad. Sci. USA, vol. 85, Apr. 1988, pp. 2444-2448.
Saitou et al., "The Neighbor-Joining Method: A New Method for Reconstructing Phylogenetic Trees1", Mol. Biol. Evol., vol. 4, No. 4, 1987, pp. 406-425.
Sambrook et al., "Molecular Cloning a Laboratory Manual; Third Edition", Cold Spring Harbor Laboratory Press, vol. 1, 2001, 2 pages.
Schweizer et al., "Identification and Characterization of Recombinant Plasmids Carrying the Complete qa Gene Cluster From *Neurospora crassa* including the qa-1+ Regulatory Gene", Proc. Natl. Acad. Sci. USA, vol. 78, No. 8, Aug. 1981, pp. 5086-5090.
Smith et al., "Comparison of Biosequences", Advances in Applied Mathematics, vol. 2, 1981, pp. 482-489.
Tamura et al., "MEGA4: Molecular Evolutionary Genetics Analysis (MEGA) Software Version 4.0", Mol. Biol. Evol., vol. 24, No. 8, 2007, pp. 1596-1599.
Thompson et al., "Clustal W: Improving the Sensitivity of Progressive Multiple Sequence Alignment through Sequence Weighting, Position-Specific Gap Penalties and Weight Matrix Choice", Nucleic Acids Research, vol. 22, No. 22, 1994, pp. 4673-4680.
Toivari et al., "Endogenous Xylose Pathway in *Saccharomyces cerevisiae*", Applied and Environmental Microbiology, vol. 70, No. 6, Jun. 2004, pp. 3681-3686.
Träff et al., "Putative Xylose and Arabinose Reductases in *Saccharomyces cerevisiae*", Yeast, vol. 19, 2002, pp. 1233-1241.
Träff-Bjerre et al., "Endogenous NADPH-Dependent Aldose Reductase Activity Influences Product Formation during Xylose Consumption in Recombinant *Saccharomyces cerevisiae*", Yeast, vol. 21, 2004, pp. 141-150.

*Primary Examiner* — Maryam Monshipouri
(74) *Attorney, Agent, or Firm* — Morrison & Foerster LLP

(57) ABSTRACT

The present disclosure provides compositions and methods related to the fermentation of xylose. Host cells having recombinant polynucleotides encoding one or more of aldose reductases, xylitol dehydrogenases, and xylulokinase are provided herein. Host cells having reduced expression of PHO13 are also provided herein. Also provided herein are uses of host cells provided herein, and methods relating to the use of xylose-containing materials.

17 Claims, 6 Drawing Sheets

XYLOSE-FERMENTING MICROORGANISM

CROSS REFERENCE TO RELATED APPLICATIONS

This application claims the benefit of U.S. Provisional Patent Application No. 61/550,333, filed Oct. 21, 2011, which is hereby incorporated by reference, in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 658012001200SEQLISTING.txt, date recorded: Oct. 19, 2012, size: 31 KB).

FIELD

The present disclosure relates to the fermentation of xylose. In particular, the present disclosure relates to compositions for the fermentation of xylose, including host cells that contain recombinant polynucleotides and polypeptides, and that optionally also have reduced expression of an endogenous gene. The disclosure further relates to methods of use of the host cells of the disclosure and methods for the fermentation of xylose-containing materials.

BACKGROUND

*Saccharomyces cerevisiae* (*S. cerevisiae*) is the primary microorganism that is currently used for biofuel production from sugars derived from plant materials. However, *S. cerevisiae* cannot ferment xylose, the second most abundant sugar in cellulosic hydrolyzates. Therefore, there is great interest in developing efficient xylose-fermenting strains of *S. cerevisiae*.

Three major approaches have been taken to attempt to metabolically engineer xylose-fermenting strains of *S. cerevisiae*. First, attempts have been made to introduce into *S. cerevisiae* heterologous genes for assimilating xylose. Genes for assimilating xylose are found in certain species of yeast which naturally have the ability to ferment xylose, such as *Schejfersomyces stipitis* (*S. stipitis*), also known as *Pichia stipitis* (*P. stipitis*). In *S. stipitis*, xylose is reduced to xylitol by NADPH or NADH-linked xylose reductase (XR) (*S. stipitis* gene XYL1 ("SsXYL1") and xylitol is subsequently oxidized to xylulose by NAD+-linked xylitol dehydrogenase (XDH) (*S. stipitis* gene XYL2 ("SsXYL2"). Xylulokinase (XK) (*S. stipitis* gene XYL3 ("SsXYL3") phosphorylates xylulose into xylulose-5-phosphate which can be metabolized through the pentose phosphate pathway (PPP). It has been hypothesized that the cofactor difference between XR and XDH can lead to cellular redox imbalance, possibly reducing xylose consumption rate as well as triggering oxidative metabolism in response to xylose. Much research has been performed to optimize the cofactor usage of XR and XDH by protein engineering, but to date, the improvement in xylose metabolism has been marginal. Many efforts in finding the best set of XR and XDH are still continuing.

Second, it has been demonstrated that introduction of xylose isomerase (XI) from bacteria and anaerobic fungi (e.g. the xylA gene) into yeast can confer xylose fermentation under anaerobic conditions. This XI pathway is one step isomerization, which has no substrate loss and no cofactor requirement. However, it is not as energetically favorable as the XR/XDH pathway, resulting in slow conversion of xylose.

Third, internal limitations of *S. cerevisiae* in metabolizing xylose have been identified which are present in *S. cerevisiae*, regardless of the type of xylose-assimilating pathway used. The introduction of xylose-specific transporters and overexpression of some genes in the PPP have improved xylose metabolism by engineered *S. cerevisiae*.

The existence of an endogenous metabolic pathway in *S. cerevisiae* for assimilation of xylose has also been suggested. Batt et al. demonstrated that wild type *S. cerevisiae* could metabolize very limited amounts of xylose, although it could not grow on xylose as a sole carbon source (Batt et al., Biotechnol. Bioeng., 28:549-553 (1986)). Through testing phenotypes of deletion mutants of putative endogenous XRs within *S. cerevisiae*, Traff et al. proposed that the *S. cerevisiae* gene GRE3 ("ScGRE3") (an aldose reductase (AR)) might encode an enzyme having xylose reductase activity (Traff et al. Yeast, 19: 1233-1241, (2002)). Additionally, it has been reported that an engineered *S. cerevisiae* strain overexpressing ScGRE3 with *S. cerevisiae* XYL2 (ScXYL2) or *S. stipitis* XYL2 (SsXYL2) grew on xylose and produced xylitol (Traff-Bjerre et al., Yeast, 21: 141-150, (2004); Toivari et al, Appl. Environ. Microbiol, 70: 3681-3686, (2004)). However, ethanol production by the engineered *S. cerevisiae* strains with ScGRE3 overexpression was not significant. Aldose reductase encoded by ScGRE3 can reduce xylose into xylitol. However, ScGRE3 AR uses only NADPH as a cofactor, unlike SsXYL1 XR, which can use either NADPH or NADH. Therefore, it has been hypothesized and experiments have suggested that overexpression of ScGRE3, rather than SsXYL1, is detrimental for xylose fermentation by *S. cerevisiae*, due to redox imbalance. Traff-Bjerre et al. reported that an *S. cerevisiae* strain overexpressing ScGRE3, SsXYL2, and the *S. cerevisiae* XK gene XKS1 ("ScXKS1") exhibited a 5 times slower xylose consumption rate as well as a lower ethanol yield, as compared to a control strain overexpressing SsXYL1, SsXYL2, and ScXKS1 (Traff-Bjerre et al. Yeast, 21: 141-150, (2004)). Toivari et al. showed that a *S. cerevisiae* strain overexpressing ScGRE3 and SsXYL2 had a lower growth rate and produced more xylitol than the strain overexpressing SsXYL1 and SsXYL2 (Toivari et al. Appl. Environ. Microbiol., 70: 3681-3686, (2004)). These results in the art suggest that overexpression of ScGRE3 is not recommended for constructing an efficient xylose-fermenting *S. cerevisiae* strain.

BRIEF SUMMARY

The present disclosure provides compositions and methods related to the metabolism of xylose.

Accordingly, certain aspects of the present disclosure provide a host cell containing: a) a recombinant polynucleotide encoding an aldose reductase; b) a recombinant polynucleotide encoding a xylitol dehydrogenase; and c) a recombinant polynucleotide encoding a xylulokinase.

In certain embodiments, the recombinant polynucleotide encoding an aldose reductase encodes a polypeptide containing an amino acid selected from (i) SEQ ID NO: 2; (ii) a sequence having at least 70% identity to SEQ ID NO: 2; and (iii) a fragment consisting of a sequence having 90% or greater identity to at least 20 consecutive amino acids of SEQ ID NO: 2. In certain embodiments, the recombinant polynucleotide encoding an aldose reductase encodes a polypeptide containing an amino acid selected from (i) SEQ ID NO: 2; (ii) a sequence having at least 70% identity to SEQ ID NO: 2; and (iii) a fragment consisting of a sequence having 90% or greater identity to at least 20 consecutive amino acids of SEQ ID NO: 2; the recombinant polynucleotide encoding a xylitol dehydrogenase encodes a polypeptide containing an amino acid selected from (i) SEQ ID NO: 6; (ii) a sequence having at least 70% identity to SEQ ID NO: 6; and (iii) a fragment consisting of a sequence having 90% or greater identity to at least 20 consecutive amino acids of SEQ ID NO: 6; and the recombinant polynucleotide encoding a xylulokinase encodes a polypeptide containing an amino acid selected from (i) SEQ ID NO: 8; (ii) a sequence having at least 70% identity to SEQ ID NO: 8; and (iii) a fragment consisting of a sequence having 90% or greater identity to at least 20 consecutive amino acids of SEQ ID NO: 8. In certain embodiments that may be combined with any of the preceding embodiments, the host cell has a modification affecting the expression of PHO13 or a PHO13 ortholog, where the modification is an insertion, deletion, and/or mutation in the PHO13 or PHO13 ortholog gene. In certain embodiments that may be combined with any of the preceding embodiments, the host cell is a *Saccharomyces cerevisiae* (*S. cerevisiae*) cell. In certain embodiments that may be combined with any of the preceding embodiments, one or more of the recombinant polynucleotides are under the control of a constitutive promoter. In certain embodiments that may be combined with any of the preceding embodiments, all of the recombinant polynucleotides are under the control of a constitutive promoter. In certain embodiments that may be combined with any of the preceding embodiments, the host cell further contains one or more recombinant polynucleotides that encode a hemicellulase. In certain embodiments that may be combined with any of the preceding embodiments, the host cell contains a recombinant polynucleotide that encodes a xylanase.

Other aspects of the present disclosure provide a method of increasing the consumption of xylose by a cell in xylose-containing material, by incubating the host cell of any of the preceding embodiments in xylose-containing material under conditions sufficient to support the expression of said recombinant polynucleotides, where the host cell consumes more xylose than a corresponding host cell lacking said recombinant polynucleotides. In certain embodiments, the host cell produces more ethanol than a corresponding host cell lacking said recombinant polynucleotides. In certain embodiments that may be combined with any of the preceding embodiments, the xylose-containing material is incubated with the host cell under conditions that support the generation of a fermentation product.

Other aspects of the present disclosure provide a method of converting a hemicellulose-containing material to fermentation product, by: a) contacting the hemicellulose-containing material with a host cell of any of the preceding embodiments where the host cell further contains one or more recombinant polynucleotides that encode a hemicellulase; and b) incubating the host cell and the hemicellulose-containing material under conditions that support the degradation of hemicellulose and the generation of a fermentation product.

In certain embodiments that may be combined with any of the preceding embodiments, the xylose-containing material is derived from hemicellulose. In certain embodiments that may be combined with any of the preceding embodiments, the hemicellulose is derived from biomass. In certain embodiments that may be combined with any of the preceding embodiments, the recombinant polynucleotide encoding an aldose reductase encodes a polypeptide containing an amino acid selected from the group consisting of (i) SEQ ID NO: 2; (ii) a sequence having at least 70% identity to SEQ ID NO: 2; and (iii) a fragment consisting of a sequence having 90% or greater identity to at least 20 consecutive amino acids of SEQ ID NO: 2. In certain embodiments that may be combined with any of the preceding embodiments, the xylose-containing material is incubated with the host cell under conditions that support the generation of a fermentation product.

Another aspect of the present disclosure provides host cells that can efficiently metabolize xylose and that contain recombinant polynucleotides encoding an aldose reductase and a xylitol dehydrogenase. Host cells disclosed herein may also contain a recombinant polynucleotide encoding a xylulokinase. Previous reports of host cells containing recombinant polynucleotides encoding the aldose reductase ScGRE3 and the xylitol dehydrogenase SsXYL2 indicated that these cells could not efficiently metabolize xylose, particularly as compared to cells containing recombinant polynucleotides encoding the xylose reductase SsXYL1 and the xylitol dehydrogenase SsXYL2 (Traff-Bjerre et al., Yeast, 21: 141-150, (2004); Toivari et al., Appl. Environ. Microbiol., 70: 3681-3686, (2004)). Disclosed herein are host cells containing recombinant polynucleotides encoding the aldose reductase ScGRE3 and the xylitol dehydrogenase SsXYL2 which, surprisingly, can efficiently metabolize xylose.

Host cells disclosed herein may also further have a modification that results in reduced expression of the phosphatase PHO13, or its ortholog, in the cell. Host cells disclosed herein containing recombinant polynucleotides which can efficiently metabolize xylose may have particular levels of enzymatic activity disclosed herein. Further provided here are methods of using host cells containing recombinant polynucleotides encoding an aldose reductase and a xylitol dehydrogenase for various processes related to xylose fermentation.

Provided herein is a host cell containing a recombinant polynucleotide encoding an aldose reductase, and a recombinant polynucleotide encoding a xylitol dehydrogenase. In some aspects, the recombinant polynucleotide encoding an aldose reductase may encode a polypeptide containing an amino acid selected from (i) SEQ ID NO: 2 (ScGRE3 amino acid); (ii) a sequence having at least 70% identity to SEQ ID NO: 2; and (iii) a fragment consisting of a sequence having 90% or greater identity to at least 20 consecutive amino acids of SEQ ID NO: 2. In some aspects, the recombinant polynucleotide encoding a xylitol dehydrogenase may encode a polypeptide containing an amino acid selected from (i) SEQ ID NO: 6 (SsXYL2 amino acid); (ii) a sequence having at least 70% identity to SEQ ID NO: 6; and (iii) a fragment consisting of a sequence having 90% or greater identity to at least 20 consecutive amino acids of SEQ ID NO: 6.

A host cell containing a recombinant polypeptide encoding an aldose reductase and a recombinant polypeptide encoding a xylitol dehydrogenase may further contain a recombinant polynucleotide encoding a xylulokinase. In some aspects, the recombinant polynucleotide encoding a xylulokinase may encode a polypeptide containing an amino acid selected from (i) SEQ ID NO: 8 (SsXYL3 amino acid); (ii) a sequence having at least 70% identity to SEQ ID NO: 8; and (iii) a fragment consisting of a sequence having 90% or greater identity to at least 20 consecutive amino acids of SEQ ID NO: 8. In some aspects, the recombinant polynucleotide encoding a xylulokinase may encode a polypeptide containing an amino acid selected from (i) SEQ ID NO: (ScXKS1 amino acid); (ii) a sequence having at least 70% identity to SEQ ID NO: 10; and (iii) a fragment consisting of a sequence having 90% or greater identity to at least 20 consecutive amino acids of SEQ ID NO: 10.

Any of the host cells provided herein may also have a modification affecting the expression of PHO13 or a PHO13 ortholog, and may have reduced expression of PHO13 or a PHO13 ortholog as compared to a corresponding host cell lacking the modification. In some aspects, host cells having a modification affecting the expression of PHO13 or a PHO13 ortholog and having reduced expression of PHO13 or a PHO13 ortholog have an insertion, deletion, and/or mutation in the PHO13 or PHO13 ortholog gene.

In some aspects, host cells provided herein are *S. cerevisiae* cells.

Recombinant polynucleotides provided herein may be under the control of a constitutive promoter, and may have a high level of expression in a cell.

Extracts from host cells provided herein may have particular levels of enzymatic activity. In one aspect, an extract from a host cell provided herein has a NADPH-dependent xylose reductase activity between 0.06 and 0.20 U/mg protein at 25° C. and pH 6.5. In another aspect, an extract from a host cell provided herein has an NAD+-dependent xylitol dehydrogenase activity between 0.5 and 2.0 U/mg protein at 25° C. and pH 9. In another aspect, an extract from a host cell provided herein has both a NADPH-dependent xylose reductase activity between 0.06 and 0.20 U/mg protein at 25° C. and pH 6.5 and an NAD+-dependent xylitol dehydrogenase activity between 0.5 and 2.0 U/mg protein at 25° C. and pH 9. In another aspect, an extract from a host cell provided herein has a NADPH-dependent xylose reductase activity between 0.06 and 0.15 U/mg protein at 25° C. and pH 6.5. In another aspect, an extract from a host cell provided herein has an NAD+-dependent xylitol dehydrogenase activity between 0.5 and 1.5 U/mg protein at 25° C. and pH 9. In another aspect, an extract from a host cell provided herein has both a NADPH-dependent xylose reductase activity between 0.06 and 0.15 U/mg protein at 25° C. and pH 6.5 and an NAD+-dependent xylitol dehydrogenase activity between 0.5 and 1.5 U/mg protein at 25° C. and pH 9.

Any of the host cells provided herein may further contain one or more recombinant polynucleotides that encode a hemicellulase, such as a xylanase.

Also provided herein is a method of increasing the growth rate of a cell in xylose-containing material, the method including incubating any of the host cells provided herein in xylose-containing material under conditions sufficient to support the expression of the recombinant polynucleotides, wherein the host cell grows at a faster rate than a corresponding host cell lacking the recombinant polynucleotides.

Also provided herein is a method of increasing the consumption of xylose by a cell in xylose-containing material, the method including incubating any of the host cells provided herein in xylose-containing material under conditions sufficient to support the expression of the recombinant polynucleotides, wherein the host cell consumes more xylose than a corresponding host cell lacking the recombinant polynucleotides.

Also provided herein is a method of increasing ethanol production by a cell in xylose-containing material, the method including incubating any of the host cells provided herein in xylose-containing material under conditions sufficient to support the expression of the recombinant polynucleotides, wherein the host cell produces more ethanol than a corresponding host cell lacking the recombinant polynucleotides.

Also provided herein is a method of decreasing acetate production by a cell in xylose-containing material, the method including incubating any of the host cells provided herein in xylose-containing material under conditions sufficient to support the expression of the recombinant polynucleotides, wherein the host cell produces less acetate than a corresponding host cell lacking the recombinant polynucleotides.

Further provided herein is method of fermenting a xylose-containing material, the method including contacting the xylose-containing material with any of the host cells provided herein, and incubating the host cell and xylose-containing material under conditions that support the generation of a fermentation product.

Also provided herein is a method of converting a hemicellulose-containing material to fermentation product, the method including contacting the hemicellulose-containing material with a host cell containing a recombinant polynucleotide encoding a hemicellulase provided herein, and incubating the host cell and the hemicellulose-containing material under conditions that support the degradation of hemicellulose and the generation of a fermentation product.

Fermentation products that may be generated by host cells provided herein include, without limitation: ethanol, n-propanol, n-butanol, iso-butanol, 3-methyl-1-butanol, 2-methyl-1-butanol, 3-methyl-1-pentanol, and octanol.

Xylose-containing material provided herein may be derived from hemicellulose. Hemicellulose may be derived from or be a part of biomass. Biomass may be derived from or be a part of plant material. Plant materials that may be used for biomass include, without limitation, *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine wood, birch wood, willow wood, aspen wood, poplar wood, and energy cane.

DETAILED DESCRIPTION

Figure 1:
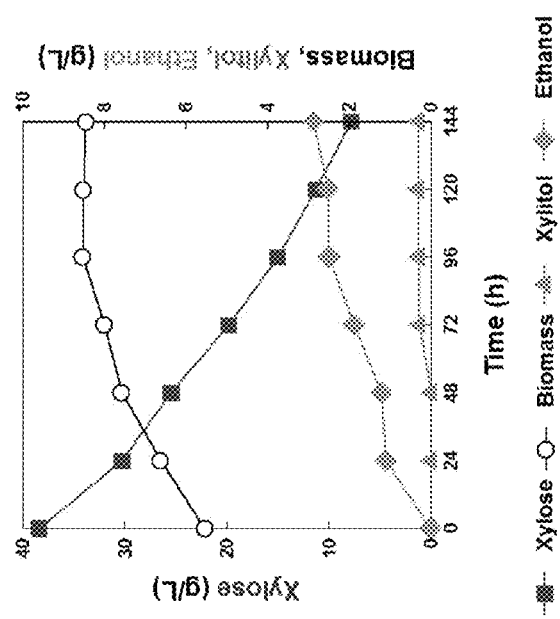
FIG. 1: Profile of xylose fermentation by *S. cerevisiae* strain DX23 (SsXYL2 and SsXYL3 in the D452-2 strain).

The present disclosure provides compositions and methods related to the metabolism of xylose.

Polypeptides of the Disclosure

The present disclosure relates to recombinant polypeptides that are involved in the metabolism of xylose. In some aspects, the disclosure relates to aldose reductases. In some aspects, the disclosure relates to xylitol dehydrogenases. In some aspects, the disclosure relates to xylulokinases.

As used herein, a "polypeptide" is a chain of consecutive polymerized amino acid residues (e.g., at least about 5 consecutive polymerized amino acid residues). As used herein, the terms "polypeptide", "protein", and "amino acid sequence" are used interchangeably.

Aldose Reductase

In some aspects, the present disclosure relates to recombinant aldose reductases. Aldose reductases are enzymes that catalyze the reduction of various aldehydes and ketones. Aldose reductases contain the National Center for Biotechnology Information (NCBI) conserved structural domain cd06660 (Aldo_ket_red), and the Pfam domain PF00248. Aldose reductases of the present disclosure catalyze the reduction of xylose (an aldehyde) to xylitol. Accordingly, aldose reductases of the present disclosure have xylose reductase activity.

An aldose reductase of the present disclosure is the polypeptide of S. cerevisiae GRE3 gene ("ScGRE3") (SEQ ID NO: 2). ScGRE3 is an NADPH-dependent aldose reductase, and it has been shown or suggested to function as a reductase of xylose, arabinose, glyceraldehyde, methylglyoxal, and β-keto esters (Traff-Bjerre et al.,Yeast, 21: 141-150, (2004)). In some aspects, ScGRE3 reduces xylose to xylitol. In some aspects, ScGRE3 is a xylose reductase.

Aldose reductases of the present disclosure include polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 2. Polypeptides of the disclosure also include polypeptides having at least 10, at least 12, at least 14, at least 16, at least 18, or at least 20 consecutive amino acids of SEQ ID NO: 2.

Aldose reductases of the present disclosure also include polypeptides that are homologs of ScGRE3. Methods for identification of polypeptides that are homologs of a polypeptide of interest are well known to one of skill in the art, as described herein. Aldose reductases disclosed herein include, without limitation, the polypeptides of NCBI Accession numbers: XP_447303.1, ADV91498.1, and ACN78427.2.

In some aspects, aldose reductases of the present disclosure have NADPH-dependent activity.

Xylitol Dehydrogenase

In some aspects, the present disclosure relates to recombinant xylitol dehydrogenases. Xylitol dehydrogenases are enzymes that catalyze the oxidation of xylitol to xylulose. Xylitol dehydrogenases contain the National Center for Biotechnology Information (NCBI) conserved structural domain cd05188 (sorbitol_DH). In some aspects, xylitol dehydrogenases have NAD+ dependent activity. A xylitol dehydrogenase of the present disclosure is the polypeptide of S. stipitis XYL2 gene ("SsXYL2") (SEQ ID NO: 6).

Xylitol dehydrogenases of the present disclosure include polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 6. Polypeptides of the disclosure also include polypeptides having at least 10, at least 12, at least 14, at least 16, at least 18, or at least 20 consecutive amino acids of SEQ ID NO: 6.

Xylitol dehydrogenases of the present disclosure also include polypeptides that are homologs of SsXYL2. Methods for identification of polypeptides that are homologs of a polypeptide of interest are well known to one of skill in the art, as described herein. Xylitol dehydrogenases disclosed herein include, without limitation, the polypeptides of NCBI Accession numbers: ACI01079.1, XP_456938.2, and ABA39795.1.

Xylulokinases

In some aspects, the present disclosure relates to recombinant xylulokinases. Xylulokinases are enzymes that catalyze the phosphorylation of xylulose to generate xylulose 5-phosphate. Xylulokinases contain the National Center for Biotechnology Information (NCBI) conserved structural domain PLN02669. In some aspects, xylulokinases use ATP to phosphorylate xylitol. A xylulokinase of the present disclosure is the polypeptide of S. stipitis XYL3 gene ("SsXYL3") (SEQ ID NO: 8).

Xylulokinases of the present disclosure include polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 8. Polypeptides of the disclosure also include polypeptides having at least 10, at least 12, at least 14, at least 16, at least 18, or at least 20 consecutive amino acids of SEQ ID NO: 8.

Xylulokinases of the present disclosure also include polypeptides that are homologs of SsXYL3. Methods for identification of polypeptides that are homologs of a polypeptide of interest are well known to one of skill in the art, as described herein. Xylulokinases disclosed herein include, without limitation, the polypeptide of S. cerevisiae XKS1 gene ("ScXKS1") (SEQ ID NO: 10) and the polypeptides of NCBI Accession numbers: XP_457985.1, EEQ44982.1, and XP_001523076.1.

Polynucleotides of the Disclosure

The present disclosure further relates to recombinant polynucleotides that encode aldose reductase, xylitol dehydrogenase, and xylulokinase polypeptides. Polynucleotides that encode a polypeptide are also referred to herein as "genes". Methods for determining the relationship between a polypeptide and a polynucleotide that encodes the polypeptide are well known to one of skill in the art. Similarly, methods of determining the polypeptide sequence encoded by a polynucleotide sequence are well known to one of skill in the art. Due to codon degeneracy, multiple different polynucleotide sequences may encode the same polypeptide.

As used herein, the terms "polynucleotide", "nucleic acid sequence", "nucleic acid", and variations thereof are generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

As used herein, more than one "polynucleotide" or "nucleic acid" may be present in a single contiguous polydeoxyribonucleotide chain/strand of DNA. Thus, a single strand of DNA (such as in a plasmid) may contain more than one "polynucleotide" or "nucleic acid", and thus, may contain sequences encoding more than one different polypeptide.

Aldose Reductases

The present disclosure relates to recombinant polynucleotides that encode an aldose reductase disclosed herein. In some aspects, the disclosure relates to polynucleotides that encode the polypeptide of ScGRE3. An example of a polynucleotide that encodes the polypeptide of ScGRE3 is the polynucleotide of SEQ ID NO: 1.

Polynucleotides of the disclosure also include polynucleotides having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 1. Polynucleotides of the disclosure also include polynucleotides that have at least 10, at least 12, at least 14, at least 16, at least 18, at least 20, at least 22, at least 24, at least 26, at least 28, or at least 30 consecutive nucleotides of SEQ ID NO: 1.

Polynucleotides of the disclosure further include fragments of polynucleotides that encode aldose reductases disclosed herein, polynucleotides that are complementary to polynucleotides that encode aldose reductases disclosed herein, and fragments of polynucleotides that are complementary to polynucleotides that encode aldose reductases disclosed herein.

Polynucleotides of the disclosure also include polynucleotides that encode aldose reductase polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 2. Polynucleotides of the disclosure also include polynucleotides that encode aldose reductase polypeptides having at least 10, at least 12, at least 14, at least 16, at least 18, or at least 20 consecutive amino acids of SEQ ID NO: 2.

Xylitol Dehydrogenases

The present disclosure relates to recombinant polynucleotides that encode a xylitol dehydrogenase disclosed herein. In some aspects, the disclosure relates to polynucleotides that encode the polypeptide of SsXYL2. An example of a polynucleotide that encodes the polypeptide of SsXYL2 is the polynucleotide of SEQ ID NO: 5.

Polynucleotides of the disclosure also include polynucleotides having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 5. Polynucleotides of the disclosure also include polynucleotides that have at least 10, at least 12, at least 14, at least 16, at least 18, at least 20, at least 22, at least 24, at least 26, at least 28, or at least 30 consecutive nucleotides of SEQ ID NO: 5.

Polynucleotides of the disclosure further include fragments of polynucleotides that encode xylitol dehydrogenases disclosed herein, polynucleotides that are complementary to polynucleotides that encode xylitol dehydrogenases disclosed herein, and fragments of polynucleotides that are complementary to polynucleotides that encode xylitol dehydrogenases disclosed herein.

Polynucleotides of the disclosure also include polynucleotides that encode xylitol dehydrogenase polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 6. Polynucleotides of the disclosure also include polynucleotides that encode xylitol dehydrogenase polypeptides having at least 10, at least 12, at least 14, at least 16, at least 18, or at least 20 consecutive amino acids of SEQ ID NO: 6.

Xylulokinases

The present disclosure relates to recombinant polynucleotides that encode a xylulokinase disclosed herein. In some aspects, the disclosure relates to polynucleotides that encode the polypeptide of SsXYL3. An example of a polynucleotide that encodes the polypeptide of SsXYL3 is SEQ ID NO: 7.

Polynucleotides of the disclosure also include polynucleotides having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 7. Polynucleotides of the disclosure also include polynucleotides that have at least 10, at least 12, at least 14, at least 16, at least 18, at least 20, at least 22, at least 24, at least 26, at least 28, or at least 30 consecutive nucleotides of SEQ ID NO: 7.

Polynucleotides of the disclosure further include fragments of polynucleotides that encode xylulokinases disclosed herein, polynucleotides that are complementary to polynucleotides that encode xylulokinases disclosed herein, and fragments of polynucleotides that are complementary to polynucleotides that encode xylulokinases disclosed herein.

Polynucleotides of the disclosure also include polynucleotides that encode xylulokinase polypeptides containing an amino acid sequence having at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 8. Polynucleotides of the disclosure also include polynucleotides that encode xylulokinase polypeptides having at least 10, at least 12, at least 14, at least 16, at least 18, or at least 20 consecutive amino acids of SEQ ID NO: 8.

In some aspects, the disclosure relates to polynucleotides that encode the polypeptide of ScXKS1. An example of a polynucleotide that encodes the polypeptide of ScXKS1 is SEQ ID NO: 9.

Polynucleotides of the disclosure also include polynucleotides having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 9. Polynucleotides of the disclosure also include polynucleotides that have at least 10, at least 12, at least 14, at least 16, at least 18, at least 20, at least 22, at least 24, at least 26, at least 28, or at least 30 consecutive nucleotides of SEQ ID NO: 9.

Sequence Homologs

As used herein, "homologs" are polypeptide or polynucleotide sequences that share a significant degree of sequence identity or similarity. Sequences that are homologs are referred to as being "homologous" to each other. Homologs include sequences that are orthologs or paralogs.

As used herein, "orthologs" are evolutionarily related polypeptide or polynucleotide sequences in different species that have similar sequences and functions, and that develop through a speciation event. Sequences that are orthologs are referred to as being "orthologous" to each other.

As used herein, "paralogs" are evolutionarily related polypeptide or polynucleotide sequences in the same organism that have similar sequences and functions, and that develop through a gene duplication event. Sequences that are paralogs are referred to as being "paralogous" to each other.

Methods of Identification of Homologous Sequences/Sequence Identity and Similarity Several different methods are known to those of skill in the art for identifying homologous sequences, including phylogenetic methods, sequence similarity analysis, and hybridization methods.

Phylogenetic Methods

Phylogenetic trees may be created for a gene family by using a program such as CLUSTAL (Thompson et al. Nucleic Acids Res. 22: 4673-4680 (1994); Higgins et al. Methods Enzymol 266: 383-402 (1996)) or MEGA (Tamura et al. Mol. Biol. & Evo. 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou & Nei, Mol. Biol. & Evo. 4:406-425 (1987)). Homologous sequences may also be identified by a reciprocal BLAST strategy. Evolutionary distances may be computed using the Poisson correction method (Zuckerkandl & Pauling, pp. 97-166 in *Evolving Genes and Proteins*, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, Genome Res. 8: 163-167 (1998)). Many specific examples exist in which gene function has been shown to correlate well with gene phylogeny (Eisen, Genome Res. 8: 163-167 (1998)). By using a phylogenetic analysis, one skilled in the art would recognize that the ability to deduce similar functions conferred by closely-related polypeptides is predictable.

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, J. Mol. Evol. 25: 351-360 (1987)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Sequence Alignment/Sequence Similarity and Identity Analysis

Methods for the alignment of sequences and for the analysis of similarity and identity of polypeptide and polynucleotide sequences are well known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Non-limiting examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, J. Mol. Biol. 48:443-453 (1970); the search-for-similarity-method of Pearson and Lipman, Proc. Natl. Acad. Sci. 85:2444-2448 (1988); the algorithm of Karlin and Altschul, Proc. Natl. Acad. Sci. USA 87:2264-2268 (1990), modified as in Karlin and Altschul, Proc. Natl. Acad. Sci. USA 90:5873-5877 (1993).

Computer implementations of these mathematical algorithms can be utilized for comparison of sequences to determine sequence identity and/or similarity. Such implementations include, but are not limited to: CLUSTAL in the PC/Gene program (available from Intelligenetics, Mountain View, Calif.); the AlignX program, version 10.3.0 (Invitrogen, Carlsbad, Calif.) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237-244 (1988); Higgins et al. CABIOS 5:151-153 (1989); Corpet et al. Nucleic Acids Res. 16:10881-90 (1988); Huang et al. CABIOS 8:155-65 (1992); and Pearson et al. Meth. Mol. Biol. 24:307-331 (1994). The BLAST programs of Altschul et al. J. Mol. Biol. 215:403-410 (1990) are based on the algorithm of Karlin and Altschul (1990) supra.

Hybridization Methods

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., Molecular Cloning: A Laboratory Manual, 3rd Ed., Vol. 1-3, Cold Spring Harbor Laboratory, Cold Spring Harbor, N.Y. ("Sambrook") (2001); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Hames and Higgins, ed., Nucleic Acid Hybridisation, A Practical Approach. Oxford, TRL Press, 73-111 (1985)).

Encompassed by the disclosure are polynucleotide sequences that are capable of hybridizing to the disclosed polynucleotide sequences, including any polynucleotide within the Sequence Listing, and fragments thereof under various conditions of stringency (see, for example, Wahl and Berger, Methods Enzymol. 152: 399-407 (1987); and Kimmel, Methods Enzymo. 152: 507-511, (1987)). In addition to the nucleotide sequences in the Sequence Listing, full length cDNA, orthologs, and paralogs of the present nucleotide sequences may be identified and isolated using well-known polynucleotide hybridization methods.

With regard to hybridization, conditions that are highly stringent, and means for achieving them, are well known in the art. See, for example, Sambrook et al. (2001) (supra); Berger and Kimmel (1987) pp. 467-469 (supra); and Anderson and Young (1985)(supra).

Hybridization experiments are generally conducted in a buffer of pH between 6.8 to 7.4, although the rate of hybridization is nearly independent of pH at ionic strengths likely to be used in the hybridization buffer (Anderson and Young (1985)(supra)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency. As a general guidelines high stringency is typically performed at $T_m$–5° C. to $T_m$–20° C., moderate stringency at $T_m$–20° C. to $T_m$–35° C. and low stringency at $T_m$–35° C. to $T_m$–50° C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m$–25° C. for DNA-DNA duplex and $T_m$–15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements that encode the present transcription factors include, for example: 6×SSC and 1% SDS at 65° C.; 50% formamide, 4×SSC at 42° C.; 0.5×SSC to 2.0×SSC, 0.1% SDS at 50° C. to 65° C.; or 0.1×SSC to 2×SSC, 0.1% SDS at 50° C.-65° C.; with a first wash step of, for example, 10 minutes at about 42° C. with about 20% (v/v) formamide in 0.1×SSC, and with, for example, a subsequent wash step with 0.2×SSC and 0.1% SDS at 65° C. for 10, 20 or 30 minutes.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Wash procedures will generally employ at least two final wash steps. Additional variations on these conditions will be readily apparent to those skilled in the art (see, for example, US Patent Application No. 20010010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 min in duration, or about 0.1×SSC, 0.1% SDS at 65° C. and washing twice for 10, 20 or 30 min. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Polynucleotide probes may be prepared with any suitable label, including a fluorescent label, a colorimetric label, a radioactive label, or the like. Labeled hybridization probes for detecting related polynucleotide sequences may be produced, for example, by oligolabeling, nick translation, end-labeling, or PCR amplification using a labeled nucleotide.

Host Cells of the Disclosure

The present disclosure further relates to host cells that contain recombinant polynucleotides encoding one or more of an aldose reductase, a xylitol dehydrogenase, and a xylulokinase.

"Host cell" and "host microorganism" are used interchangeably herein to refer to a living biological cell that can be transformed via insertion of recombinant DNA or RNA. Such recombinant DNA or RNA can be in an expression vector.

Any prokaryotic or eukaryotic host cell may be used in the present disclosure so long as it remains viable after being transformed with a sequence of nucleic acids. Preferably, the host cell is not adversely affected by the transduction of the necessary nucleic acid sequences, the subsequent expression of the proteins (e.g., transporters), or the resulting intermediates.

In some aspects, the host is a fungal strain. "Fungi" as used herein includes the phyla Ascomycota, Basidiomycota, Chytridiomycota, and Zygomycota as well as the Oomycota and all mitosporic fungi.

In certain embodiments, the fungal host is a yeast strain. "Yeast" as used herein refers to any single cell fungus that reproduces asexually by budding or division, and it includes fungi of both Ascomycota and Basidiomycota.

In certain embodiments, the yeast host is of the genus *Saccharomyces, Schizosaccharomyces, Leucosporidium, Dekkera/Brettanomyces, Zygosaccharomyces, Yarrowia, Hansenula, Kluyveromyces, Scheffersomyces (Pichia),* or *Candida*.

In certain embodiments, the yeast host is of the species *Saccharomyces cerevisiae, Saccharomyces monacensis, Saccharomyces bayanus, Saccharomyces pastorianus, Saccharomyces carlsbergensis, Leucosporidium frigidum, Saccharomyces telluris, Candida slooffi, Schizosaccharomyces pombe, Kluyveromyces marxiamus, Kluyveromyces lactis, Kluyveromyces fragilis, Scheffersomyces (Pichia) stipitis, Sporotrichum thermophile, Candida shehatae, Candida tropicalis, Hansenula polymorpha (Pichia angusta), Brettanomyces custersii,* or *Zygosaccharomyces rouxii*.

*Saccharomyces* sp. may include industrial *Saccharomyces* strains. Argueso et al. describe the genome structure of an industrial *Saccharomyces* strain commonly used in bioethanol production, as well as specific gene polymorphisms that are important for bioethanol production (Argueso et al., Genome Research, 19: 2258-2270, (2009)).

The host cells of the present disclosure may be genetically modified in that recombinant nucleic acids have been introduced into the host cells, and as such the genetically modified host cells do not occur in nature. The suitable host cell is one capable of expressing one or more recombinant nucleic acid constructs encoding one or more proteins for different functions.

"Recombinant nucleic acid" or "heterologous nucleic acid" or "recombinant polynucleotide", "recombinant nucleotide" or "recombinant DNA" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid. Specifically, the present disclosure describes the introduction of an expression vector into a host cell, wherein the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. As used herein, the term "recombinant polypeptide" refers to a polypeptide generated from a "recombinant nucleic acid" or "heterologous nucleic acid" or "recombinant polynucleotide", "recombinant nucleotide" or "recombinant DNA" as described above. Recombinant polynucleotides and polypeptides also include polynucleotides or polypeptides that are isolated from their natural cellular environment.

In some aspects, the host cell naturally produces a protein encoded by a polynucleotide of the disclosure. A gene encoding the desired protein may be heterologous to the host cell or the gene may be endogenous to the host cell but is operatively linked to a heterologous promoters and/or control region which results in the higher expression of the gene in the host cell.

Host Cell Components

In some aspects, host cells of the disclosure contain recombinant polynucleotides encoding an aldose reductase and a xylitol dehydrogenase. In some aspects, host cells of the disclosure contain recombinant polynucleotides encoding an aldose reductase, a xylitol dehydrogenase, and a xyluulokinase. In some aspects, host cells of the disclosure contain recombinant polynucleotides encoding ScGRE3 aldose reductase and SsXYL2 xylitol dehydrogenase. In some aspects, host cells of the disclosure contain recombinant polynucleotides encoding ScGRE3 aldose reductase, SsXYL2 xylitol dehydrogenase, and SsXYL3 xylulokinase. In some aspects, a host cell that contains recombinant polynucleotides encoding an aldose reductase, xylitol dehydrogenase, and/or xylulokinase contains a greater amount of aldose reductase, xylitol dehydrogenase, and/or xylulokinase protein, respectively, than a corresponding host cell that does not contain recombinant polynucleotides encoding an aldose reductase, xylitol dehydrogenase, or xylulokinase, respectively. When a protein or polynucleotide is produced or maintained in a host cell at an amount greater than normal, the protein or nucleic acid is "overexpressed." In some aspects, host cells of the disclosure overexpress one or more of an aldose reductase, xylitol dehydrogenase, or xylulokinase. The present disclosure further is directed to cells that are modified and that have a greater level of one or more of an aldose reductase, xylitol dehydrogenase, or xylulokinase than a corresponding cell that is not modified.

In some aspects, host cells of the disclosure contain a recombinant polynucleotide containing the polynucleotide sequence of SEQ ID NO: 1.

In some aspects, host cells of the disclosure contain a recombinant polynucleotide containing the polynucleotide sequence of SEQ ID NO: 5.

In some aspects, host cells of the disclosure contain a recombinant polynucleotide containing the polynucleotide sequence of SEQ ID NO: 7.

In some aspects, host cells of the disclosure contain a recombinant polynucleotide containing the polynucleotide sequence of SEQ ID NO: 9.

Host cells of the disclosure may also contain one or more recombinant polynucleotides that encode a hemicellulase. Hemicellulases include, without limitation, exoxylanases, endoxylanases, α-arabinofuranosidases, α-glucuronidases, β-xylosidases, and acetyl xylan esterases.

Host cells of the disclosure may further contain one or more recombinant polynucleotides that encode a polypeptide in a biochemical pathway related to the production of a biofuel. In some aspects, a host cell contains a recombinant polynucleotide encoding a polypeptide in a biochemical pathway involved in the production of ethanol, n-propanol, n-butanol, iso-butanol, 3-methyl-1-butanol, 2-methyl-1-butanol, 3-methyl-1-pentanol, and/or octanol.

Host Cells Having Reduced Expression of PHO13

In some embodiments, any of the host cells provided herein may have reduced expression of PHO13.

PHO13 is an alkaline phosphatase that has protein phosphatase activity. In *S. cerevisiae* PHO13 has the systematic name YDL236W. In *S. cerevisiae*, PHO13 may have the amino acid sequence of SEQ ID NO: 12 and may be encoded by the polynucleotide of SEQ ID NO: 11. Reduction of PHO13 expression in *S. cerevisiae* has been shown to increase xylose fermentation by a host cell that overexpresses recombinant *Schejfersomyces stipitis* (*S. stipitis*) XYL1 xylose reductase, XYL2 xylitol dehydrogenase, and XYL3 xylulokinase polypeptides (U.S. Pat. No. 7,285,403). However, as shown in Example 5 below, surprisingly, reducing expression of PHO13 improves xylose fermentation by cells overexpressing ScGRE3, SsXYL2, and SsXYL3 to a much greater extent than reducing expression of PHO13 improves xylose fermentation by cells overexpressing SsXYL1, SsXYL2, and SsXYL3.

As used herein, a host cell having "reduced expression" of PHO13 has reduced PHO13 enzymatic activity, as compared to PHO13 activity in a corresponding non-modified cell. "Reduced expression" may be caused by any mechanism that directly or indirectly reduces PHO13 enzymatic activity in a cell. Thus, host cells having reduced expression of PHO13 include, without limitation, cells having an insertion, deletion, or mutation in the gene encoding PHO13 which reduces or eliminates the activity of the translated PHO13 protein, cells having an insertion, deletion, or mutation in the gene encoding PHO13 which results in lower amounts of PHO13 protein in the cell, cells having an insertion, deletion, or mutation in the promoter region of the gene encoding PHO13 which reduces or eliminates the transcription of RNA encoding PHO13, cells containing nucleic acids which interfere with the stability or translation of mRNA encoding the PHO13 protein (e.g. antisense RNA, siRNA, RNAi, etc.), and cells containing molecules that inhibit the activity of PHO13 proteins.

In one aspect, cells having reduced expression of PHO13 have a deletion of the entire PHO13-coding region, and do not produce PHO13 polypeptides. In another aspect, cells having reduced expression of PHO13 encode a PHO13 polypeptide having a glycine to arginine mutation in amino acid number 166 (G166R) of SEQ ID NO: 12. In another aspect, cells having reduced expression of PHO13 encode a PHO13 polypeptide having a glycine to aspartic acid mutation in amino acid number 253 (G253D) of SEQ ID NO: 12. In another aspect, cells having reduced expression of PHO13 encode a PHO13 polypeptide having a threonine to alanine mutation in amino acid number 306 (T306A) of SEQ ID NO: 12. In another aspect, cells having reduced expression of PHO13 encode a PHO13 polypeptide containing only amino acids 1-216 of SEQ ID NO: 12. In such cells, the failure to express amino acids 217-312 of SEQ ID NO: 12 may be for any reason, including a mutation to result in a premature stop codon in the PHO13 gene, or a deletion of part of the gene. In another aspect, cells having reduced expression of PHO13 encode a PHO13 polypeptide containing only amino acids 1-203 of SEQ ID NO: 12. In such cells, the failure to express amino acids 204-312 of SEQ ID NO: 12 may be for any reason, including a mutation to result in a premature stop codon in the PHO13 gene, or a deletion of part of the gene. Cells of the disclosure also include non-5, cerevisiae cells having mutations/deletions corresponding to the above mutations/deletions in PHO13 orthologs.

In some aspects, host cells of the disclosure include host cells having reduced expression of PHO13 or a PHO13 ortholog and containing recombinant polynucleotides encoding an aldose reductase and a xylitol dehydrogenase. In some aspects, host cells of the disclosure include host cells having reduced expression of PHO13 or a PHO13 ortholog and containing recombinant polynucleotides encoding an aldose reductase, a xylitol dehydrogenase, and a xylulokinase. In some aspects, host cells of the disclosure include host cells having reduced expression of PHO13 and containing recombinant polynucleotides encoding ScGRE3 aldose reductase and SsXYL2 xylitol dehydrogenase. In some aspects, host cells of the disclosure include host cells having reduced expression of PHO13 and containing recombinant polynucleotides encoding ScGRE3 aldose reductase, SsXYL2 xylitol dehydrogenase, and SsXYL3 xylulokinase.

Cells having reduced expression of PHO13 may be prepared by any mechanism known to those of skill in the art for reduction of expression of a gene. For example, a gene encoding PHO13 may be mutated or deleted using homologous recombination or through the use of a disruption cassette. Techniques for reducing the expression of a gene are provided, for example, in Abelson et. al., *Guide to Yeast Genetics and Molecular Biology, Part A, Volume* 194, Academic Press (2004) and Xiao, W. ed., *Yeast Protocols*, Humana Press, 2nd ed. (2005).

Host cells provided herein having reduced expression of PHO13 include any host cell species disclosed herein. In some aspects, *S. cerevisiae* host cells having reduced expression of PHO13 are provided herein. Also provided herein are non-5, cerevisiae cells having reduced expression an ortholog of *S. cerevisiae* PHO13. Methods for the identification of nucleic acids and polypeptides that are orthologous to *S. cerevisiae* PHO13 are well known to one of skill in the art, as described herein.

Host Cell Enzymatic Activity

In some aspects, host cells of the disclosure have xylose reductase and xylitol dehydrogenase activity. In some aspects, host cells of the disclosure have xylose reductase, xylitol dehydrogenase, and xylulokinase activity.

Typically, xylose reductase and/or xylitol dehydrogenase activity in a cell is determined by measuring the xylose reductase and/or xylitol dehydrogenase activity present in a crude cellular extract from multiple cells of a cell of interest. To obtain a crude cellular extract, cells are first exposed to a condition to lyse the cells, and then the lysed cells are treated by a method to remove insoluble material. The remaining, soluble material is crude cellular extract. Generally, cells in late exponential growth phase when cell density becomes 50% of maximum are used for preparation of a crude cell extract.

Yeast cells may be lysed by any method for cell lysis, including mechanical or enzymatic means. In some aspects, yeast cells are lysed with glass beads. In some aspects, yeast cells are lysed with sonication. In some aspects, yeast cells are lysed with a French press. In some aspects, yeast cells are lysed with Y-PER yeast protein extraction reagent (Thermo Scientific, Rockford Ill.). Insoluble material may be removed from lysed cells by any method for the removal of insoluble material from soluble material. In some aspects, insoluble material is removed from lysed yeast cells by centrifugation. In some aspects, insoluble material is removed from lysed yeast cells by filtration.

Xylose reductase activity is enzymatic activity that converts xylose to xylitol. In some aspects, the xylose reductase activity is NADPH-dependent. Xylose reductase enzymatic activity in a sample may be measured by monitoring the concentration of NADPH in a sample that may contain xylose reductase. Since xylose reductase consumes NADPH during its enzymatic activity, measurement of a change in NADPH concentration provides a means of monitoring xylose reductase activity. Typically, NADPH concentration is determined by use of a spectrophotometer to measure absorbance of 340 nm UV light in a NADPH-containing sample. NADPH absorbs 340 nm UV light, whereas NADP+ does not. Thus, measurement of absorbance of 340 nm UV light provides a means for monitoring the conversion of NADPH to NADP+ in a sample. In some aspects, absorbance of 340 nm light by a NADPH-containing sample may be measured for a period of time, in order to monitor NADPH consumption in a sample over a period of time. Typically, when measuring the consumption of NADPH in a sample, a second reaction mixture lacking a necessary component of the reaction (e.g. xylose) is also prepared, for use as a control reaction. Once data regarding NADPH consumption by a sample containing xylose reductase is obtained, the xylose reductase activity level in a sample can be determined. Xylose reductase activity may be determined according to the formula: delta absorbance at 340 nm/min*conversion factor (μmol NADPH/Abs)*1/mg protein.

Xylitol dehydrogenase activity is enzymatic activity that converts xylitol to xylulose. In some aspects, the xylitol dehydrogenase activity is NAD+-dependent. Xylitol dehydrogenase enzymatic activity in a sample may be measured by monitoring the concentration of NADH in a sample that may contain xylitol dehydrogenase. Since xylitol dehydrogenase generates NADH during its enzymatic activity, measurement of a change in NADH concentration provides a means of monitoring xylitol dehydrogenase activity. Typically, NADH concentration is determined by use of a spectrophotometer to measure absorbance of 340 nm UV light in a NADH-containing sample. NADH absorbs 340 nm UV light, whereas NAD+ does not. Thus, measurement of absorbance of 340 nm UV light provides a means for monitoring the generation of NADH from NAD+ in a sample. In some aspects, absorbance of 340 nm light by a NADH-containing sample may be measured for a period of time, in order to monitor NADH generation in a sample over a period of time. Typically, when measuring the generation of NADH in a sample, a second reaction mixture lacking a necessary component of the reaction (e.g. xylitol) is also prepared, for use as a control reaction. Once data regarding NADH generation by a sample containing xylitol dehydrogenase is obtained, the xylitol dehydrogenase activity level in a sample can be determined. Xylitol dehydrogenase activity may be calculated according to the formula: delta absorbance (Abs) at 340 nm/min*conversion factor (μmol NADH/Abs)*1/mg protein.

Activity of an enzyme may be defined in "Units" (U). A Unit of enzyme activity is the amount of enzyme required to generate 1 micromole of enzyme product in 1 minute. Thus, for example, a U of xylose reductase is the amount of xylose reductase required to generate 1 micromole of xylitol from xylose in 1 minute. Similarly, a U of xylitol dehydrogenase is the amount of xylitol dehydrogenase required to generate 1 micromole of xylulose from xylitol in 1 minute.

Units of xylose reductase or xylitol dehydrogenase enzymatic activity may also be determined per a quantity of protein which contains xylose reductase and/or xylitol dehydrogenase enzymes. In some aspects, xylose reductase and/or xylitol dehydrogenase activity is determined per a quantity of protein of crude extract from cells that contain xylose reductase and/or xylitol dehydrogenase enzymes. To determine a quantity of protein in a sample, any method for the measurement of protein may be used. Methods for the quantitation of protein in a sample are well-known in the art and include, without limitation, the Bradford assay, the bicinchoninic acid (BCA) assay, and the Lowry assay.

In some aspects, Units of xylose reductase and/or xylitol dehydrogenase activity in crude extract from a host yeast cell is determined according to the following procedure: 1) Exponentially growing yeast cells are harvested, and treated with Y-PER (Thermo Scientific, Rockford Ill.) per the manufacturer's instructions, and then centrifuged, in order to generate a crude cell extract; 2) The crude cell extract is analyzed for xylose reductase and/or xylitol dehydrogenase activity by monitoring absorbance at 340 nm of a sample containing the crude cell extract, NADPH or NAD+, respectively, and xylose or xylitol, respectively. The reactions are carried out at 25° C. and pH 6.5 for the xylose reductase activity and at 25° C. and pH 9 for the xylitol dehydrogenase activity. Also, control reactions are performed. Activity of enzymes is determined according to the formula: delta absorbance (Abs) at 340 nm/min*conversion factor (μmol NADH or NADPH/Abs)*1/mg protein; 3). The concentration of protein in the sample is determined by a biochemical assay such as the BCA method. 4) Once an activity level of xylose reductase or xylitol dehydrogenase in a defined amount of protein sample is determined, the Units of xylose reductase or xylitol dehydrogenase activity per milligram protein is calculated.

In some aspects, provided herein are host cells that have xylose reductase and xylitol dehydrogenase activity. In some aspects, crude extract from multiple cells of a host cell of the disclosure that are in exponential growth phase has xylose reductase activity greater than 0.06 U/mg protein. In some aspects, crude extract from multiple cells of a host cell of the disclosure that are in exponential growth phase has xylose reductase activity between 0.06-0.2 U/mg protein. In some aspects, crude extract from multiple cells of a host cell of the disclosure that are in exponential growth phase has xylose reductase activity between 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein. In some aspects, crude extract from multiple cells of a host cell of the disclosure that are in exponential growth phase has xylitol dehydrogenase activity between greater than 0.5 U/mg protein. In some aspects, crude extract from multiple cells of a host cell of the disclosure that are in exponential growth phase has xylitol dehydrogenase activity between 0.5-2 U/mg protein. In some aspects, crude extract from multiple cells of a host cell of the disclosure that are in exponential growth phase has xylitol dehydrogenase activity between 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein. In some aspects, crude extract from multiple cells of a host cell of the disclosure that are in exponential growth phase has xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein and xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein. In some aspects, crude extract from multiple cells of a host cell of the disclosure that are in exponential growth phase has xylose reductase activity greater than 0.06, or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein and xylitol dehydrogenase activity greater than 0.5, or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein.

In some aspects, provided herein are host cells that have recombinant nucleic acids encoding ScGRE3 and SsXYL2, and that have xylose reductase and xylitol dehydrogenase activity. In some aspects, crude extract from multiple cells of a host cell of the disclosure having recombinant nucleic acids encoding ScGRE3 and SsXYL2 that are in exponential growth phase has xylose reductase activity greater than 0.06 U/mg protein. In some aspects, crude extract from multiple cells of a host cell of the disclosure having recombinant nucleic acids encoding ScGRE3 and SsXYL2 that are in exponential growth phase has xylose reductase activity between 0.06-0.2 U/mg protein. In some aspects, crude extract from multiple cells of a host cell of the disclosure having recombinant nucleic acids encoding ScGRE3 and SsXYL2 that are in exponential growth phase has xylose reductase activity between 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein. In some aspects, crude extract from multiple cells of a host cell of the disclosure having recombinant nucleic acids encoding ScGRE3 and SsXYL2 that are in exponential growth phase has xylitol dehydrogenase activity greater than 0.5 U/mg protein. In some aspects, crude extract from multiple cells of a host cell of the disclosure having recombinant nucleic acids encoding ScGRE3 and SsXYL2 that are in exponential growth phase has xylitol dehydrogenase activity between 0.5-2 U/mg protein. In some aspects, crude extract from multiple cells of a host cell of the disclosure having recombinant nucleic acids encoding ScGRE3 and SsXYL2 that are in exponential growth phase has xylitol dehydrogenase activity between 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein. In some aspects, crude extract from multiple cells of a host cell of the disclosure having recombinant nucleic acids encoding ScGRE3 and SsXYL2 that are in exponential growth phase has xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein and xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein. In some aspects, crude extract from multiple cells of a host cell of the disclosure having recombinant nucleic acids encoding ScGRE3 and SsXYL2 that are in exponential growth phase has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein and xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein.

In the values provided herein for xylose reductase and xylitol dehydrogenase activity, the enzymatic assays are carried out at 25° C. In the values provided herein for xylose reductase activity, the pH of the assay is 6.5. In the values provided herein for xylitol dehydrogenase activity, the pH of the assay is 9. The values provided herein are for NADPH-dependent xylose-reductase activity. The values provided herein are for NAD+-dependent xylitol dehydrogenase activity.

Molecules related to xylose reductase and/or xylitol dehydrogenase activity may also be analyzed additional methods. For example, the concentration of acetate, glucose, xylose, xylitol, ethanol, glycerol and other molecules in a sample may be determined by high performance liquid chromatography (HPLC). Thus, xylose reductase and/or xylitol dehydrogenase activity may additionally or alternatively be monitored by measuring the concentration in a sample of substrates or products of xylose reductase and/or xylitol dehydrogenase activity. Xylose reductase and/or xylitol dehydrogenase activity may also or alternatively be monitored by measuring the concentration in a sample of molecules related to xylose reductase and/or xylitol dehydrogenase activity, such as fermentation products.

In some aspects, provided herein are host cells that contain recombinant nucleic acids encoding an aldose reductase and a xylitol dehydrogenase and that have reduced expression of PHO13 or a PHO13 ortholog. Also provided herein are host cells that contain recombinant nucleic acids encoding an aldose reductase and a xylitol dehydrogenase and that have reduced expression of PHO13 or a PHO13 ortholog, and wherein crude extract from multiple cells of the host cell that are in exponential growth phase has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In some aspects, provided herein are host cells that contain recombinant nucleic acids encoding ScGRE3 aldose reductase and SsXYL2 xylitol dehydrogenase, and that have reduced expression of PHO13 or a PHO13 ortholog. Also are provided herein are host cells that contain recombinant nucleic acids encoding ScGRE3 aldose reductase and SsXYL2 xylitol dehydrogenase, and that have reduced expression of PHO13 or a PHO13 ortholog, and wherein crude extract from multiple cells of the host cell that are in exponential growth phase has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In some aspects, provided herein are host cells that contain recombinant nucleic acids encoding an aldose reductase and a xylitol dehydrogenase and a xylulokinase and that have reduced expression of PHO13 or a PHO13 ortholog. Also provided herein are host cells that contain recombinant nucleic acids encoding an aldose reductase and a xylitol dehydrogenase and a xylulokinase and that have reduced expression of PHO13 or a PHO13 ortholog, and wherein crude extract from multiple cells of the host cell that are in exponential growth phase has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In some aspects, provided herein are host cells that contain recombinant nucleic acids encoding ScGRE3 aldose reductase, SsXYL2 xylitol dehydrogenase, and SsXYL3 xylulokinase, and that have reduced expression of PHO13 or a PHO13 ortholog. Also are provided herein are host cells that contain recombinant nucleic acids encoding ScGRE3 aldose reductase, SsXYL2 xylitol dehydrogenase, and SsXYL3 xylulokinase, and that have reduced expression of PHO13 or a PHO13 ortholog, and wherein crude extract from multiple cells of the host cell that are in exponential growth phase has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

Methods of Producing and Culturing Host Cells of the Disclosure

Methods of producing and culturing host cells of the disclosure may include the introduction or transfer of expression vectors containing the recombinant polynucleotides of the disclosure into the host cell. Such methods for transferring expression vectors into host cells are well known to those of ordinary skill in the art. For example, one method for transforming cells with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Cells also may be transformed through the use of spheroplasts (Schweizer, M, Proc. Natl. Acad. Sci., 78: 5086-5090 (1981). Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

In some cases, cells are prepared as protoplasts or spheroplasts prior to transformation. Protoplasts or spheroplasts may be prepared, for example, by treating a cell having a cell wall with enzymes to degrade the cell wall. Fungal cells may be treated, for example, with zymolyase or chitinase.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids which together contain the total DNA to be introduced into the genome of the host, or a transposon may be used.

The vectors preferably contain one or more selectable markers which permit easy selection of transformed hosts. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Selectable markers for use in fungal host cells include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Suitable markers for *S. cerevisiae* hosts include, for example, ADE2, HIS3, LEU2, LYS2, MET3, TRP1, and URA3.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should contain a sufficient number of nucleic acids, such as 100 to 10,000 base pairs, 400 to 10,000 base pairs, or 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further contain an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo.

The vector may further contain a promoter for regulation of expression of a recombinant nucleic acid in the vector. Promoters for the regulation of expression of a gene are well-known in the art, and include constitutive promoters, and inducible promoters. Promoters are described, for example, in Sambrook, et al. *Molecular Cloning: A Laboratory Manual*, 3rd edition, Cold Spring Harbor Laboratory Press, (2001). In some aspects, vectors for use in *Saccharomyces* spp. may include the TDH1 or PGK1 promoter, which are strong and constitutive promoters.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 2001, supra).

Once the host cell has been transformed with the expression vector, the host cell is allowed to grow. Growth of a host cell in a medium may involve the process of fermentation. Methods of the disclosure may include culturing the host cell such that recombinant nucleic acids in the cell are expressed. Media, temperature ranges and other conditions suitable for growth are known in the art.

Applications

Methods of Increasing Cell Growth

Provided herein are methods for increasing the growth rate of a cell in a xylose-containing material. In one aspect, a method for increasing the growth rate of a cell in a xylose-containing material includes increasing the expression of an aldose reductase and a xylitol dehydrogenase in a cell. In one aspect, a method for increasing the growth rate of a cell in a xylose-containing material includes increasing the expression of an aldose reductase, a xylitol dehydrogenase, and a xylulokinase in a cell. In one aspect, a method for increasing the growth rate of a cell in a xylose-containing material includes increasing the expression of the aldose reductase ScGRE3 and the xylitol dehydrogenase SsXYL2 in a cell. In one aspect, a method for increasing the growth rate of a cell in a xylose-containing material includes increasing the expression of the aldose reductase ScGRE3, the xylitol dehydrogenase SsXYL2, and the xylulokinase SsXYL3 in a cell. Cells having an increased expression of an aldose reductase and a xylitol dehydrogenase may have an increased growth rate in xylose-containing material as compared with a corresponding cell not having increased expression of an aldose reductase and a xylitol dehydrogenase. To increase the growth rate of a cell in xylose-containing material, in one aspect, a cell containing recombinant polynucleotides encoding an aldose reductase and a xylitol dehydrogenase is incubated in xylose-containing material under conditions sufficient to support the expression of the aldose reductase and xylitol dehydrogenase.

In one aspect, a method for increasing the growth rate of a cell in a xylose-containing material includes increasing the expression of an aldose reductase and a xylitol dehydrogenase in a cell, and decreasing expression of PHO13 in the cell. In one aspect, a method for increasing the growth rate of a cell in a xylose-containing material includes increasing the expression of an aldose reductase, a xylitol dehydrogenase, and a xylulokinase in a cell, and decreasing expression of PHO13 in the cell. In one aspect, a method for increasing the growth rate of a cell in a xylose-containing material includes increasing the expression of the aldose reductase ScGRE3 and the xylitol dehydrogenase SsXYL2 in a cell, and decreasing expression of PHO13 in the cell. In one aspect, a method for increasing the growth rate of a cell in a xylose-containing material includes increasing the expression of the aldose reductase ScGRE3, the xylitol dehydrogenase SsXYL2, and the xylulokinase SsXYL3 in a cell, and decreasing expression of PHO13 in the cell. Cells having an increased expression of an aldose reductase and a xylitol dehydrogenase and a decreased expression of PHO13 may have an increased growth rate in xylose-containing material as compared with a corresponding cell not having increased expression of an aldose reductase and a xylitol dehydrogenase. To increase the growth rate of a cell in xylose-containing material, in one aspect, a cell containing recombinant nucleic acids encoding an aldose reductase and a xylitol dehydrogenase and having reduced expression of PHO13 is incubated in xylose-containing material under conditions sufficient to support the expression of the aldose reductase and xylitol dehydrogenase, and the reduced expression of PHO13.

In one aspect, a method for increasing the growth rate of a cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing the growth rate of a cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing the growth rate of a cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing the growth rate of a cell in a xylose-containing material includes increasing the expression of ScGRE3 and SsXYL2 in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing the growth rate of a cell in a xylose-containing material includes increasing the expression of ScGRE3 and SsXYL2 in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-

1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing the growth rate of a cell in a xylose-containing material includes increasing the expression of ScGRE3 and SsXYL2 in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing the growth rate of a cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing the growth rate of a cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing the growth rate of a cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing the growth rate of a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing the growth rate of a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing the growth rate of a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In any of the methods disclosed herein for increasing the growth rate of a cell in a xylose-containing material, the method may further include decreasing the expression of PHO13 or a PHO13 ortholog in the cell. Expression of PHO13 or a PHO13 ortholog may be decreased by any method disclosed herein.

Method of Increasing Xylose Consumption, Increasing Ethanol Production, and/or Decreasing Acetate Formation Provided herein are methods for increasing xylose consumption, increasing ethanol production, and/or decreasing acetate formation by a cell in a xylose-containing material. In one aspect, a method for increasing xylose consumption, increasing ethanol production, and/or decreasing acetate formation by a cell in a xylose-containing material includes increasing the expression of an aldose reductase and a xylitol dehydrogenase in a cell. In one aspect, a method for increasing xylose consumption, increasing ethanol production, and/or decreasing acetate formation by a cell in a xylose-containing material includes increasing the expression of an aldose reductase, a xylitol dehydrogenase, and a xylulokinase in a cell. In one aspect, a method for increasing xylose consumption, increasing ethanol production, and/or decreasing acetate formation by a cell in a xylose-containing material includes increasing the expression of the aldose reductase ScGRE3 and the xylitol dehydrogenase SsXYL2 in a cell. In one aspect, a method for increasing xylose consumption, increasing ethanol production, and/or decreasing acetate formation by a cell in a xylose-containing material includes increasing the expression of the aldose reductase ScGRE3, the xylitol dehydrogenase SsXYL2, and the xylulokinase SsXYL3 in a cell. Cells having an increased expression of an aldose reductase and a xylitol dehydrogenase may have increased xylose consumption, increased ethanol production, and/or decreased acetate formation in xylose-containing material as compared with a corresponding cell not having increased expression of an aldose reductase and a xylitol dehydrogenase. To increase xylose consumption, increase ethanol production, and/or decrease acetate formation by a cell in xylose-containing material, in one aspect, a cell containing recombinant nucleic acids encoding an aldose reductase and a xylitol dehydrogenase is incubated in xylose-containing material under conditions sufficient to support the expression of the aldose reductase and xylitol dehydrogenase.

In one aspect, a method for increasing xylose consumption, increasing ethanol production, and/or decreasing acetate formation by a cell in a xylose-containing material includes increasing the expression of an aldose reductase and a xylitol dehydrogenase in a cell, and decreasing expression of PHO13 in the cell. In one aspect, a method for increasing xylose consumption, increasing ethanol production, and/or decreasing acetate formation by a cell in a xylose-containing material includes increasing the expression of an aldose reductase, a xylitol dehydrogenase, and a xylulokinase in a cell, and decreasing expression of PHO13 in the cell. In one aspect, a method for increasing xylose consumption, increasing ethanol production, and/or decreasing acetate formation by a cell in a xylose-containing material includes increasing the expression of the aldose reductase ScGRE3 and the xylitol dehydrogenase SsXYL2 in a cell, and decreasing expression of PHO13 in the cell. In one aspect, a method for increasing xylose consumption, increasing ethanol production, and/or decreasing acetate formation by a cell in a xylose-containing material includes increasing the expression of the aldose reductase ScGRE3, the xylitol dehydrogenase SsXYL2, and the xylulokinase SsXYL3 in a cell, and decreasing expression of PHO13 in the cell. Cells having an increased expression of an aldose reductase and a xylitol dehydrogenase and having decreased expression of PHO13 may have increased xylose consumption, increased ethanol production, and/or decreased acetate formation in xylose-containing material as compared with a corresponding cell not having increased expression of an aldose reductase and a xylitol dehydrogenase, and decreased expression of PHO13. To increase xylose consumption, increase ethanol production, and/or decrease acetate formation by a cell in xylose-containing material, in one aspect, a cell containing recombinant polynucleotides encoding an aldose reductase and a xylitol dehydrogenase and having reduced expression of PHO13 is incubated in xylose-containing material under conditions sufficient to support the expression of the aldose reductase and xylitol dehydrogenase and the reduced expression of PHO13.

In one aspect, a method for increasing xylose consumption, increasing ethanol production, and/or decreasing acetate formation by cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing xylose consumption, increasing ethanol production, and/or decreasing acetate formation by a cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing xylose consumption, increasing ethanol production, and/or decreasing acetate formation by a cell in a xylose-containing material includes increasing the expression of an aldose reductase and a xylitol dehydrogenase in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing xylose consumption, increasing ethanol production, and/or decreasing acetate formation by a cell in a xylose-containing material includes increasing the expression of ScGRE3 and SsXYL2 in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing xylose consumption, increasing ethanol production, and/or decreasing acetate formation by a cell in a xylose-containing material includes increasing the expression of ScGRE3 and SsXYL2 in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing xylose consumption, increasing ethanol production, and/or decreasing acetate formation by a cell in a xylose-containing material includes increasing the expression of ScGRE3 and SsXYL2 in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing xylose consumption, increasing ethanol production, and/or decreasing acetate formation by cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing xylose consumption, increasing ethanol production, and/or decreasing acetate formation by a cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing xylose consumption, increasing ethanol production, and/or decreasing acetate formation by a cell in a xylose-containing material includes increasing the expression of an aldose reductase, a xylitol dehydrogenase, and a xylulokinase in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for increasing xylose consumption, increasing ethanol production, and/or decreasing acetate formation by a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for increasing xylose consumption, increasing ethanol production, and/or decreasing acetate formation by a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for increasing xylose consumption, increasing ethanol production, and/or decreasing acetate formation by a cell in a xylose-containing material includes increasing the expression of ScGRE3, SsXYL2, and SsXYL3 in a cell, wherein crude extract from multiple cells of the host cell that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In any of the methods disclosed herein for increasing xylose consumption, increasing ethanol production, and/or decreasing acetate formation by a cell in a xylose-containing material, the method may further include decreasing the expression of PHO13 or a PHO13 ortholog in the cell. Expression of PHO13 or a PHO13 ortholog may be decreased by any method disclosed herein.

Methods of Converting Xylose-Containing Materials to Fermentation Product

Further provided herein are methods for converting xylose-containing materials to a fermentation production. In one aspect, a method for converting a xylose-containing material into a fermentation product includes the steps of culturing the xylose-containing material with a fermentative microorganism having increased expression of an aldose reductase and a xylitol dehydrogenase under conditions sufficient to produce a fermentation product. In one aspect, a method for converting a xylose-containing material into a fermentation product includes the steps of culturing the xylose-containing material with a fermentative microorganism having increased expression of an aldose reductase, a xylitol dehydrogenase, and a xylulokinase under conditions sufficient to produce a fermentation product. In one aspect, a method for converting a xylose-containing material into a fermentation product includes the steps of culturing the xylose-containing material with a fermentative microorganism having increased expression of the aldose reductase ScGRE3 and the xylitol dehydrogenase SsXYL2 under conditions sufficient to produce a fermentation product. In one aspect, a method for converting a xylose-containing material into a fermentation product includes the steps of culturing the xylose-containing material with a fermentative microorganism having increased expression of the aldose reductase ScGRE3, the xylitol dehydrogenase SsXYL2, and the xylulokinase SsXYL3 under conditions sufficient to produce a fermentation product. Cells having an increased expression of an aldose reductase and a xylitol dehydrogenase may have an increased rate of conversion of a xylose-containing material to fermentation product as compared with a corresponding cell not having increased expression of an aldose reductase and a xylitol dehydrogenase. To increase the rate of conversion of a xylose-containing material to fermentation product, in one aspect, a cell containing recombinant polynucleotides encoding an aldose reductase and a xylitol dehydrogenase is incubated in xylose-containing material under conditions sufficient to support the expression of the aldose reductase and xylitol dehydrogenase.

In one aspect, a method for converting a xylose-containing material into a fermentation product includes the steps of culturing the xylose-containing material with a fermentative microorganism having increased expression of an aldose reductase and a xylitol dehydrogenase, and having reduced expression of PHO13 under conditions sufficient to produce a fermentation product. In one aspect, a method for converting a xylose-containing material into a fermentation product includes the steps of culturing the xylose-containing material with a fermentative microorganism having increased expression of an aldose reductase, a xylitol dehydrogenase, and a xylulokinase, and having reduced expression of PHO13 under conditions sufficient to produce a fermentation product. In one aspect, a method for converting a xylose-containing material into a fermentation product includes the steps of culturing the xylose-containing material with a fermentative microorganism having increased expression of the aldose reductase ScGRE3 and the xylitol dehydrogenase SsXYL2, and having reduced expression of PHO13 under conditions sufficient to produce a fermentation product. In one aspect, a method for converting a xylose-containing material into a fermentation product includes the steps of culturing the xylose-containing material with a fermentative microorganism having increased expression of the aldose reductase ScGRE3, the xylitol dehydrogenase SsXYL2, and the xylulokinase SsXYL3, and having reduced expression of PHO13 under conditions sufficient to produce a fermentation product. Cells having an increased expression of an aldose reductase and a xylitol dehydrogenase and having reduced expression of PHO13 may have an increased rate of conversion of a xylose-containing material to fermentation product as compared with a corresponding cell not having increased expression of an aldose reductase and a xylitol dehydrogenase and decreased expression of PHO13. To increase the rate of conversion of a xylose-containing material to fermentation product, in one aspect, a cell containing recombinant polynucleotides encoding an aldose reductase and a xylitol dehydrogenase and having reduced expression of PHO13 is incubated in xylose-containing material under conditions sufficient to support the expression of the aldose reductase and xylitol dehydrogenase and the reduced expression of PHO13.

In one aspect, a method for converting a xylose-containing material into a fermentation product includes the steps of culturing the xylose-containing material with a fermentative microorganism having increased expression of an aldose reductase and a xylitol dehydrogenase under conditions sufficient to produce a fermentation product, wherein crude extract from multiple cells of the fermentative microorganism that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for converting a xylose-containing material into a fermentation product includes the steps of culturing the xylose-containing material with a fermentative microorganism having increased expression of an aldose reductase and a xylitol dehydrogenase under conditions sufficient to produce a fermentation product, wherein crude extract from multiple cells of the fermentative microorganism that are in exponential growth phase has NADPH-dependent has xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for converting a xylose-containing material into a fermentation product includes the steps of culturing the xylose-containing material with a fermentative microorganism having increased expression of an aldose reductase and a xylitol dehydrogenase under conditions sufficient to produce a fermentation product, wherein crude extract from multiple cells of the fermentative microorganism that are in exponential growth phase has NADPH-dependent has xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for converting a xylose-containing material into a fermentation product includes the steps of culturing the xylose-containing material with a fermentative microorganism having increased expression of ScGRE3 and SsXYL2 under conditions sufficient to produce a fermentation product, wherein crude extract from multiple cells of the fermentative microorganism that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for converting a xylose-containing material into a fermentation product includes the steps of culturing the xylose-containing material with a fermentative microorganism having increased expression of ScGRE3 and SsXYL2 under conditions sufficient to produce a fermentation product, wherein crude extract from multiple cells of the fermentative microorganism that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for converting a xylose-containing material into a fermentation product includes the steps of culturing the xylose-containing material with a fermentative microorganism having increased expression of ScGRE3 and SsXYL2 under conditions sufficient to produce a fermentation product, wherein crude extract from multiple cells of the fermentative microorganism that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for converting a xylose-containing material into a fermentation product includes the steps of culturing the xylose-containing material with a fermentative microorganism having increased expression of an aldose reductase, a xylitol dehydrogenase, and a xylulokinase under conditions sufficient to produce a fermentation product, wherein crude extract from multiple cells of the fermentative microorganism that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for converting a xylose-containing material into a fermentation product includes the steps of culturing the xylose-containing material with a fermentative microorganism having increased expression of an aldose reductase, a xylitol dehydrogenase, and a xylulokinase under conditions sufficient to produce a fermentation product, wherein crude extract from multiple cells of the fermentative microorganism that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for converting a xylose-containing material into a fermentation product includes the steps of culturing the xylose-containing material with a fermentative microorganism having increased expression of an aldose reductase, a xylitol dehydrogenase, and a xylulokinase under conditions sufficient to produce a fermentation product, wherein crude extract from multiple cells of the fermentative microorganism that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In one aspect, a method for converting a xylose-containing material into a fermentation product includes the steps of culturing the xylose-containing material with a fermentative microorganism having increased expression of ScGRE3, SsXYL2, and SsXYL3 under conditions sufficient to produce a fermentation product, wherein crude extract from multiple cells of the fermentative microorganism that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9. In one aspect, a method for converting a xylose-containing material into a fermentation product includes the steps of culturing the xylose-containing material with a fermentative microorganism having increased expression of ScGRE3, SsXYL2, and SsXYL3 under conditions sufficient to produce a fermentation product, wherein crude extract from multiple cells of the fermentative microorganism that are in exponential growth phase has NADPH-dependent xylose reductase activity between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9. In one aspect, a method for converting a xylose-containing material into a fermentation product includes the steps of culturing the xylose-containing material with a fermentative microorganism having increased expression of ScGRE3, SsXYL2, and SsXYL3 under conditions sufficient to produce a fermentation product, wherein crude extract from multiple cells of the fermentative microorganism that are in exponential growth phase has NADPH-dependent xylose reductase activity greater than 0.06 or between 0.06-0.1, 0.06-0.12, 0.06-0.15, 0.06-0.20, 0.06-0.30, 0.06-0.40, 0.06-0.50, 0.06-0.60, 0.06-0.70, 0.06-0.80, 0.06-0.90, 0.08-0.1, 0.08-0.12, 0.08-0.15, 0.08-0.20, 0.1-0.12, 0.1-0.15, 0.1-0.20, 0.08-0.3, 0.08-0.4, 0.08-0.5, or 0.08-0.6 U/mg protein at 25° C. and pH 6.5 and NAD+-dependent xylitol dehydrogenase activity greater than 0.5 or between 0.5-2, 0.2-0.5, 0.2-1, 0.2-1.2, 0.2-1.5, 0.2-2, 0.2-3, 0.5-1, 0.5-1.2, 0.5-1.5, 0.5-3, 1-1.2, 1-1.5, 1-2, 1-3, 1.5-2, or 1.5-3 U/mg protein at 25° C. and pH 9.

In any of the methods disclosed herein for converting xylose-containing materials to a fermentation production, the method may further include decreasing the expression of PHO13 or a PHO13 ortholog in the fermentative organism and/or culturing the xylose-containing material with a fermentative organism having reduced expression of PHO13 or a PHO13 ortholog. Expression of PHO13 or a PHO13 ortholog may be decreased by any method disclosed herein.

Fermentation products that may be produced from xylose-containing materials include, without limitation, ethanol, n-propanol, n-butanol, iso-butanol, 3-methyl-1-butanol, 2-methyl-1-butanol, 3-methyl-1-pentanol, and octanol.

Fermentative organisms include, without limitation, *Saccharomyces* spp.

Methods of Consolidated Bioprocessing

Further provided herein are methods for converting hemicellulose-containing materials to a fermentation production, by consolidated bioprocessing. Consolidated bioprocessing combines enzyme generation, biomass hydrolysis, and biofuel production into a single stage.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding an aldose reductase and a xylitol dehydrogenase and having reduced expression of PHO13 under conditions sufficient to support expression of the polynucleotides and the reduced expression of PHO13; B) incubating the hemicellulose-containing material with the cell having recombinant polynucleotides encoding one or more hemicellulases and having recombinant polynucleotides encoding an aldose reductase and a xylitol dehydrogenase and having reduced expression of PHO13 under conditions sufficient to support expression of the polynucleotides and the reduced expression of PHO13, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding an aldose reductase, a xylitol dehydrogenase, and a xylulokinase and having reduced expression of PHO13 under conditions sufficient to support expression of the polynucleotides and the reduced expression of PHO13; B) incubating the hemicellulose-containing material with the cell having recombinant polynucleotides encoding one or more hemicellulases and having recombinant polynucleotides encoding an aldose reductase, a xylitol dehydrogenase, and a xylulokinase and having reduced expression of PHO13 under conditions sufficient to support expression of the polynucleotides and the reduced expression of PHO13, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding an aldose reductase and a xylitol dehydrogenase under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9; B) incubating the hemicellulose-containing material with the cell having recombinant polynucleotides encoding one or more hemicellulases and having recombinant polynucleotides encoding an aldose reductase and a xylitol dehydrogenase under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding the aldose reductase ScGRE3 and the xylitol dehydrogenase SsXYL2 and having reduced expression of PHO13 under conditions sufficient to support expression of the polynucleotides and the reduced expression of PHO13; B) incubating the hemicellulose-containing material with the cell having recombinant polynucleotides encoding one or more hemicellulases and having recombinant polynucleotides encoding the aldose reductase ScGRE3 and the xylitol dehydrogenase SsXYL2 and having reduced expression of PHO13 under conditions sufficient to support expression of the polynucleotides and the reduced expression of PHO13, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding the aldose reductase ScGRE3, the xylitol dehydrogenase SsXYL2, and the xylulokinase SsXYL3 and having reduced expression of PHO13 under conditions sufficient to support expression of the polynucleotides and the reduced expression of PHO13; B) incubating the hemicellulose-containing material with the cell having recombinant polynucleotides encoding one or more hemicellulases and having recombinant polynucleotides encoding the aldose reductase ScGRE3, the xylitol dehydrogenase SsXYL2, and the xylulokinase SsXYL3 and having reduced expression of PHO13 under conditions sufficient to support expression of the polynucleotides and the reduced expression of PHO13, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding the aldose reductase ScGRE3 and the xylitol dehydrogenase SsXYL2 under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9; B) incubating the hemicellulose-containing material with the cell having recombinant polynucleotides encoding one or more hemicellulases and having recombinant polynucleotides encoding the aldose reductase ScGRE3 and the xylitol dehydrogenase SsXYL2 under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9, under conditions that support hemicellulose degradation and xylose fermentation, in order to produce a fermentation product.

In another aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding an aldose reductase, a xylitol dehydrogenase, and a xylulokinase under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9; B) incubating the hemicellulose-containing material with the cell having recombinant polynucleotides encoding one or more hemicellulases and having recombinant polynucleotides encoding an aldose reductase, a xylitol dehydrogenase, and a xylulokinase under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9, under conditions that support hemicellulose degradation and xylose fermentation, in order to produce a fermentation product.

In one aspect, a method for converting a hemicellulose-containing material into a fermentation product by consolidated bioprocessing includes the steps of: A) contacting a hemicellulose-containing material with a cell having recombinant polynucleotides encoding one or more hemicellulases and having recombinant polynucleotides encoding the aldose reductase ScGRE3, the xylitol dehydrogenase SsXYL2, and the xylulokinase SsXYL3 under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9; B) incubating the hemicellulose-containing material with the cell having recombinant polynucleotides encoding one or more hemicellulases and having recombinant polynucleotides encoding the aldose reductase ScGRE3, the xylitol dehydrogenase SsXYL2, and the xylulokinase SsXYL3 under conditions sufficient to support expression of the polynucleotides, wherein crude extract from multiple cells of the cell that are in exponential growth phase has NADPH-dependent xylose reductase activity between 0.06-0.2 U/mg protein at 25° C. and pH 6.5 and NAD+-dependent xylitol dehydrogenase activity between 0.5-2 U/mg protein at 25° C. and pH 9, under conditions that support hemicellulose degradation and xylose fermentation, in order to produce a fermentation product.

Fermentation products that may be produced from xylose obtained from the degradation of hemicellulose-containing materials include, without limitation, ethanol, n-propanol, n-butanol, iso-butanol, 3-methyl-1-butanol, 2-methyl-1-butanol, 3-methyl-1-pentanol, and octanol.

In any of the methods disclosed herein for converting hemicellulose-containing materials to a fermentation production by consolidated bioprocessing, the method may further include decreasing the expression of PHO13 or a PHO13 ortholog in the cell and/or incubating the hemicellulose-containing material with a cell having decreased expression of PHO13 or a PHO13 ortholog. Expression of PHO13 or a PHO13 ortholog may be decreased by any method disclosed herein.

EXAMPLES

The following Examples are merely illustrative and are not meant to limit any aspects of the present disclosure in any way.

Example 1

Xylose Metabolism by an Engineered *S. cerevisiae* without Introducing Xylose Reductase from *Scheffersomyces stipitis* (*Pichia stipitis*)

In order to determine if *S. cerevisiae* can assimilate xylose without introducing XYL1 from *S. stipitis* into *S. cerevisiae*, an expression cassette containing only XYL2 and XYL3 from *S. stipitis* was integrated into *S. cerevisiae* strain D452-2, and the resulting transformant was named DX23. We tested if the engineered strain (DX23) would metabolize xylose as a sole carbon source. With high cell density inoculation (optical density (OD) 30), the DX23 strain was able to consume xylose very slowly (about 30 g/l of xylose was consumed in 6 days). Interestingly, the DX23 strain did not accumulate xylitol at all. Only cell growth and ethanol production (3 g/L) were observed. This result indicates that the *S. cerevisiae* strain DX23, which does not contain XYL1 from *S. stipitis*, can ferment xylose using endogenous enzymes in *S. cerevisiae* for converting xylose into xylitol.

Example 2

Construction of an Engineered *S. cerevisiae* Strain Over-Expressing ScGRE3

We selected GRE3 from *S. cerevisiae* as a putative xylose reductase enabling xylose fermentation with overexpression of SsXYL2 and SsXYL3, and over-expressed it in *S. cerevisiae*. Two almost identical expression cassettes containing either SsXYL1 or ScGRE3 with SsXYL2 and SsXYL3 were integrated into *S. cerevisiae* strain D452-2. The resulting transformants were named as DX123 (SsXYL1, SsXYL2, and SsXYL3) and DGX23 (ScGRE3, SsXYL2, and SsXYL3). Both engineered strains showed similar levels of xylitol dehydrogenase activity (Table 1). A big difference was that in vitro XR activity of DGX23 was observed only when NADPH was added as a cofactor, while in vitro XR activity of DX123 was observed using both NADPH and NADH as cofactors. The NADPH-dependency of ScGRE3 XR activity is consistent with a previous report that determined XR activities and cofactor dependencies of ScGRE3 and SsXYL1 after ScGRE3 or SsXYL1 overexpression in *S. cerevisiae* (Traff et al., Yeast, 21: 141-150, (2004)).

TABLE 1

Xylose reductase and xylitol dehydrogenase activity of DX123 and DGX23. Number values are Units (U) of activity/mg protein of crude cellular extract.

|   | NADPH-XR | NADH-XR | XDH |
|---|---|---|---|
| DX123 | 0.037 ± 0.002 | 0.116 ± 0.019 | 0.926 ± 0.073 |
| DGX23 | 0.084 ± 0.010 | Not detected | 1.156 ± 0.007 |

In this and other Examples, the xylose reductase and xylitol dehydrogenase activities were calculated according to the formula: delta absorbance (Abs) at 340 nm/min*conversion factor (μmol NADPH or NADH/Abs)*1/mg protein. The conversion factors were: μmol of NADPH/Abs at 340 nm=0.241; μmol of NADH/Abs at 340 nm=0.223.

As a sample calculation, the data and values used to determine the NADPH-specific xylose reductase activity of DGX23 for Table 1 is provided in Table 2.

TABLE 2

Data and values used to determine NADPH-specific xylose reductase activity of DGX23 (measurements were performed in triplicate).

|   | variables | | conversion factor | calculated (Unit = μmol/min) |
|---|---|---|---|---|
|   | r (dAbs/min) | protein (mg) | (constant value) f (umol/Abs) | Unit/mg (r * f/protein) |
| 1 | 0.012 | 0.0469 | 0.241 | 0.062 |
| 2 | 0.020 | 0.0493 | 0.241 | 0.098 |
| 3 | 0.020 | 0.0522 | 0.241 | 0.092 |
| Average | | | | 0.084 ± 0.010 |

Example 3

Xylose Fermentation by Engineered *S. cerevisiae* Over-Expressing ScGRE3

Figure 2:
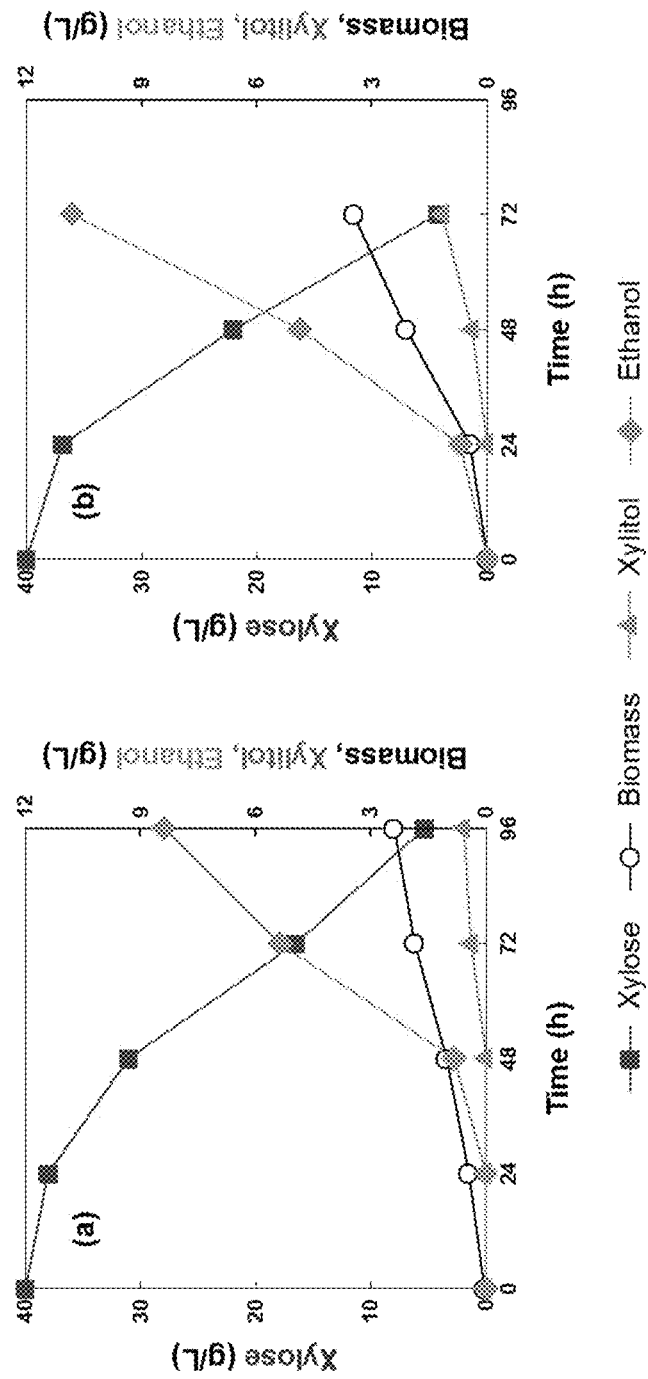
FIG. 2: Profile of xylose fermentation by (A) *S. cerevisiae* strain DX123 (SsXYL1, SsXYL2 and SsXYL3 in the D452-2 strain) and (B) *S. cerevisiae* strain DGX23 (ScGRE3, SsXYL2 and SsXYL3 in the D452-2 strain).

We compared xylose fermentation phenotypes of engineered *S. cerevisiae* strains expressing either ScGRE3 aldose reductase or SsXYL1 xylose reductase along with SsXYL2 XDH and SsXYL3 XK using 40 g/L of xylose as a sole carbon source. Both the engineered strains were able to ferment xylose and produce ethanol with decent yields when they were inoculated around OD=1 (FIG. 1). Interestingly, the ScGRE3 AR overexpressing-strain (DGX23) was able to ferment 40 g/L of xylose completely earlier (within 72 vs. 96 hours), with higher ethanol yield (0.30 vs. 0.24 g ethanol/g xylose), than the SsXYL1 XR-overexpressing strain (DX123). Cell growth of the DGX23 strain was also faster than DX123 (FIG. 2).

Figure 3:
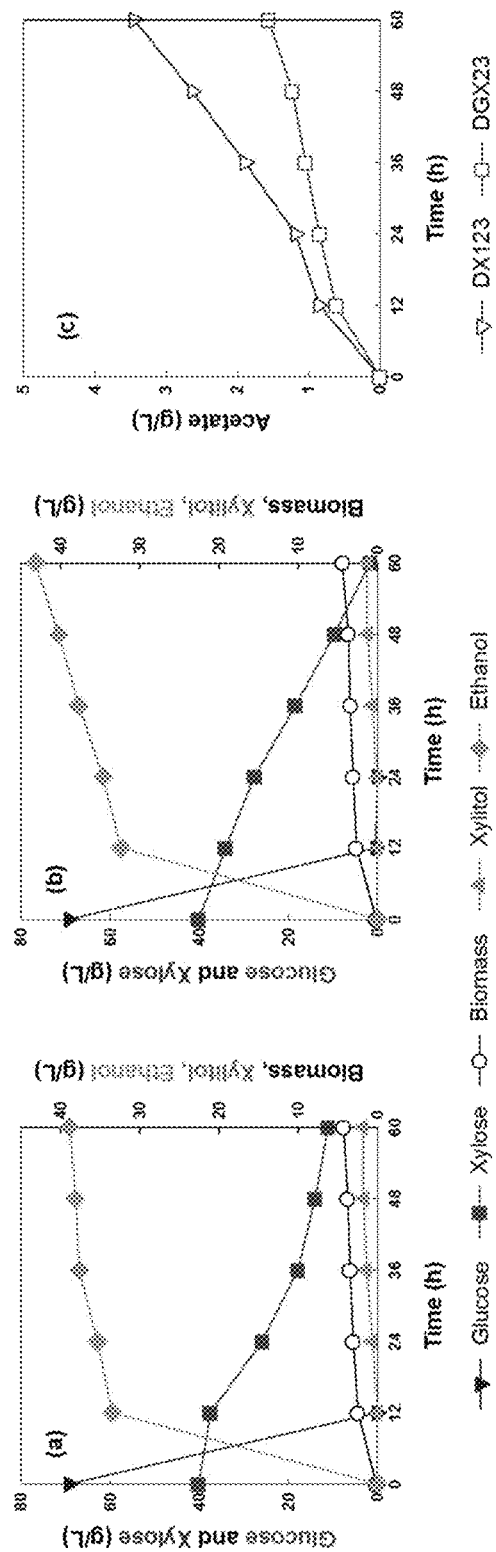
FIG. 3: Profile of fermentation of a mixture of 70 g/l of glucose and 40 g/l of xylose by (A) *S. cerevisiae* strain DX123 (SsXYL1, SsXYL2 and SsXYL3 in the D452-2 strain) and (B) *S. cerevisiae* strain DGX23 (ScGRE3, SsXYL2 and SsXYL3 in the D452-2 strain); (C) comparison of acetate production by DX123 and DGX23 during fermentation of the mixture of 70 g/l of glucose and 40 g/l of xylose.

We also examined fermentation characteristics of the both strains in a mixture of glucose and xylose. The amounts of glucose (70 g/L) and xylose (40 g/L) reflected average composition of cellulose and hemicelluose in lignocellulsic biomass. Both DX123 and DGX23 were able to consume glucose within 12 hours. After consuming glucose preferentially before xylose utilization, the DGX23 strain showed continuous xylose consumption and ethanol production (FIG. 3B), while the DX123 strain exhibited slower xylose consumption rates between 24 and 36 hours (FIG. 3A). In contrast to previous studies which have reported higher acetate production when ScGRE3 is overexpressed as compared to the overexpression of SsXYL1, we observed that DX123 produced higher amounts of acetate than DGX23 during fermentations of both xylose and a mixture of glucose and xylose (FIGS. 2 and 3). Therefore, acetate-accumulating strain DX123 was not able to produce ethanol continuously, and nor was it able to utilize xylose completely within 60 hours. In contrast, DGX23 consumed all sugars within 60 hours, and produced 44 g/l of ethanol at yield of 0.4 (g/g sugars).

TABLE 3

Fermentation parameters of DX123 and DGX23 in the conditions tested in this study.
In this table, $Y_{EtOH}$: ethanol yield (g ethanol g xylose$^{-1}$); $P_{EtOH}$: ethanol productivity (g ethanol h$^{-1}$); and $P_{EtOH}$*: specific ethanol productivity (g ethanol h$^{-1}$ g cell$^{-1}$).

|  |  | $Y_{EtOH}$ | $P_{EtOH}$ | $P_{EtOH}$* |
|---|---|---|---|---|
| YPX40 | DX123 | 0.24 | 0.09 | 0.08 |
|  | DGX23 | 0.30 | 0.11 | 0.07 |
| YPD70X40 | DX123 | 0.36 | 0.65 | 0.22 |
|  | DGX23 | 0.40 | 0.72 | 0.25 |

Example 4

GRE3 Overexpression in a Different Strain Background

Figure 4:
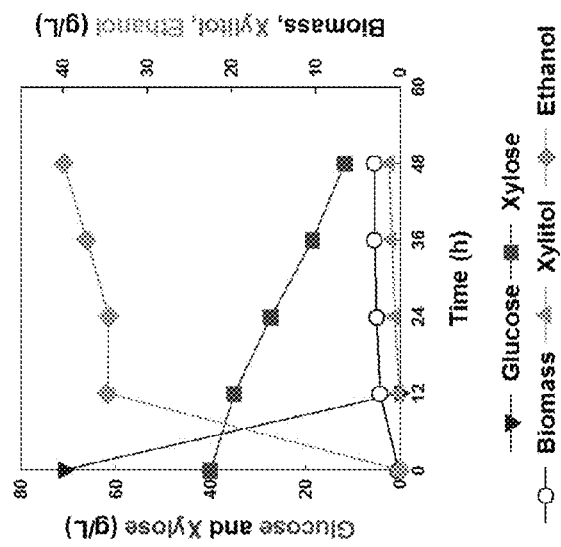
FIG. 4: Profile of fermentation of a mixture of 70 g/l of glucose and 40 g/l of xylose by CGX23 (ScGRE3, SsXYL2 and SsXYL3 in the CEN.PK2-1D strain).

Our fermentation results by an engineered *S. cerevisiae* strain overexpressing ScGRE3 are different from previous reports that *S. cerevisiae* strains over-expressing ScGRE3 were not able to ferment xylose efficiently. One possibility is that the host strain background (D452-2) of *S. cerevisiae* strains used in Examples 1-3 resulted in the phenotypes different from previous reports of *S. cerevisiae* strains overexpressing ScGRE3. Therefore, we cross-validated our results through introducing the identical cassette expressing ScGRE3 into *S. cerevisiae* CEN.PK2-1D, a laboratory strain which has been extensively used for xylose fermenation study. After transforming the identical expression cassette that was used for making DGX23 into the CEN.PK2-1D strain, a transformant was obtained and named as CGX23 (ScGRE3, SsXYL2, and SsXYL3 in CEN.PK2-1D). When a mixture of glucose and xylose was used for fermentation experiments, the CGX23 strain showed a very similar phenotype to DGX23 (FIG. 4). After fast consumption of glucose, the CGX23 strain showed continous xylose consumption and ethanol production. In addition, as with DGX23, extensive acetate accumulation was not observed. This result confirm that overexpression of ScGRE3 along with overexpressions of SsXFL2 and SsXYL3 is a alternative strategy for constructing engineered *S. cerevisiae* capable of fermenting xylose efficiently.

Materials and Methods:
Materials and Methods used for Examples 1-4 include:
Strains and Plasmids In this study, strains *S. cerevisiae* D452-2 (MATa leu2 ura3 his3) and *S. cerevisiae* CEN.PK2-1D (MATá leu2 ura3 trp1 his3) were used as host cells. The SsXYL1 or ScGRE3, SsXYL2 and SsXYL3 genes were expressed by strong and consecutive promoters such as TDH1 and PGK1. The PGK1 promoter was used for expressing SsXYL2 to maximize the expression level of SsXYL2. Three types of yeast plasmids were used: 1) pSR6-X23 (PGK1$_P$-SsXYL2-PGK1$_T$, and TDH1$_P$-SsXYL3-TDH1$_T$ in pRS306), 2) pSR6-X123 (TDH1$_P$-SsXYL1-TDH1$_T$, PGK1$_P$-SsXYL2-PGK1$_T$, and TDH1$_P$-SsXYL3-TDH1$_T$ in pRS306), and 3) pSR6-GX23 (TDH1$_P$-ScGRE3-TDH1$_T$, PGK1$_P$-SsXYL2-PGK1$_T$, and TDH1$_P$-SsXYL3-TDH1$_T$ in pRS306). By integrating the plasmids to the URA3 locus of *S. cerevisiae* D452-2, the DX23, DX123, and DGX23 strains were constructed.

Enzymatic Activity Analysis

The expression of SsXYL1 or ScGRE3 and SsXYL2 was confirmed by measuring enzymatic activities of xylose reductase and xylitol dehydrogenase in crude enzyme extracts. Since wild type strains showed only basal levels to each assay, we assumed that enzymatic activities measured in the engineered strains were resulted by the introduction and/or the over-expression of the genes. Exponentially growing cells in glucose were harvested and treated with Y-PER Yeast Protein Extraction Reagent (Thermo Scientific, Rockford Ill.) as the manufacturer recommended. The resulting crude enzyme solution was used for the following assays. Xylose reductase activities were measured in 1 ml of reaction solution containing 0.7 ml of 50 mM phosphate buffer (pH 6.5), 0.1 ml of enzyme solution, 0.1 ml of 2 mM NADPH, and 0.1 ml of 1 M xylose. The solution without xylose was incubated for 1 min at 25° C. for equilibrium. After adding xylose, the reactions were monitored for 2 min at 340 nm by a spectrophotometer. Xylitol dehydrogenase activities were also measured in the same manner using 50 mM Tris buffer (pH 9), 2 mM NAD+, and 1 M xylitol.

Fermentation

Strains were grown in 5 ml of YP medium (10 g/l of yeast extract and 20 g/l of peptone) containing 20 g/l of D-glucose (YPD) at 30° C. for 24 hours. The grown cultures were centrifuged and resuspended to 50 ml of YP medium containing 40 g/l of D-xylose (YPX) or YP medium containing 70 g/l of D-glucose and 40 g/l of D-xylose (YPDX). All fermentation experiments were started with the initial OD 1 and incubated at 30° C. and at 100 rpm.

HPLC Analysis

Glucose, xylose, xylitol, glycerol, acetate and ethanol concentrations were determined by high performance liquid chromatography (HPLC, Agilent Technologies 1200 Series) equipped with a refractive index detector using a Rezex ROA-Organic Acid H+ (8%) column (Phenomenex Inc., Torrance, Calif.). The column was eluted with 0.005 N of $H_2SO_4$ at a flow rate of 0.6 ml/min at 50° C.

Example 5

GRE3 Overexpression in a Cell Having Reduced Expression of PHO13

The PHO13 gene was deleted in DX123 (SsXYL1, SsXYL2, and SsXYL3) and DGX23 (ScGRE3, SsXYL2, and SsXYL3) cells (discussed in Examples 2-3). The PHO13 gene of each strain was deleted by substitution with KanMX4 construct (derived from the pFA6-kanMX4 plasmid, whose KanMX4 expression renders yeast resistance to geneticin (G418)), and the resulting strains were selected on YPD containing G418 (200 µg/ml) (an antibiotic).

Figure 5:
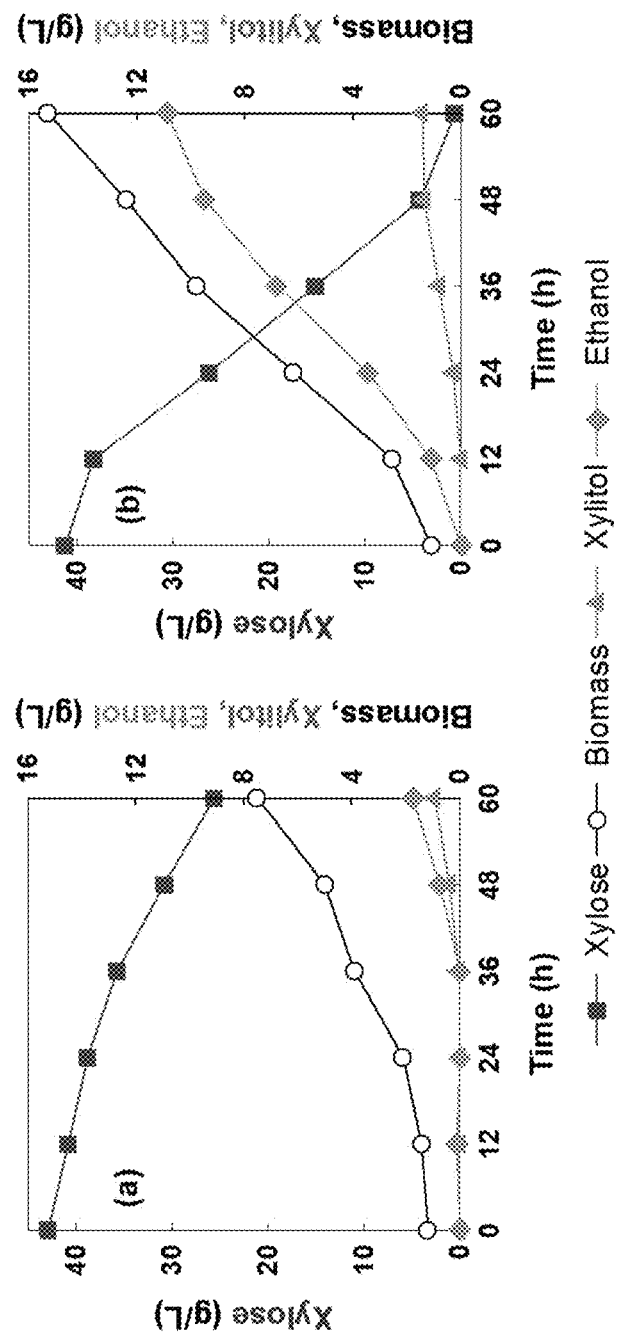
FIG. 5: The profile of xylose fermentation by DGX23 (ScGRE3, SsXYL2 and SsXYL3), with and without PHO13 gene deletion (Δpho13). (A) xylose fermentation by DGX23; (B) xylose fermentation by DGX23 Δpho13.
Figure 6:
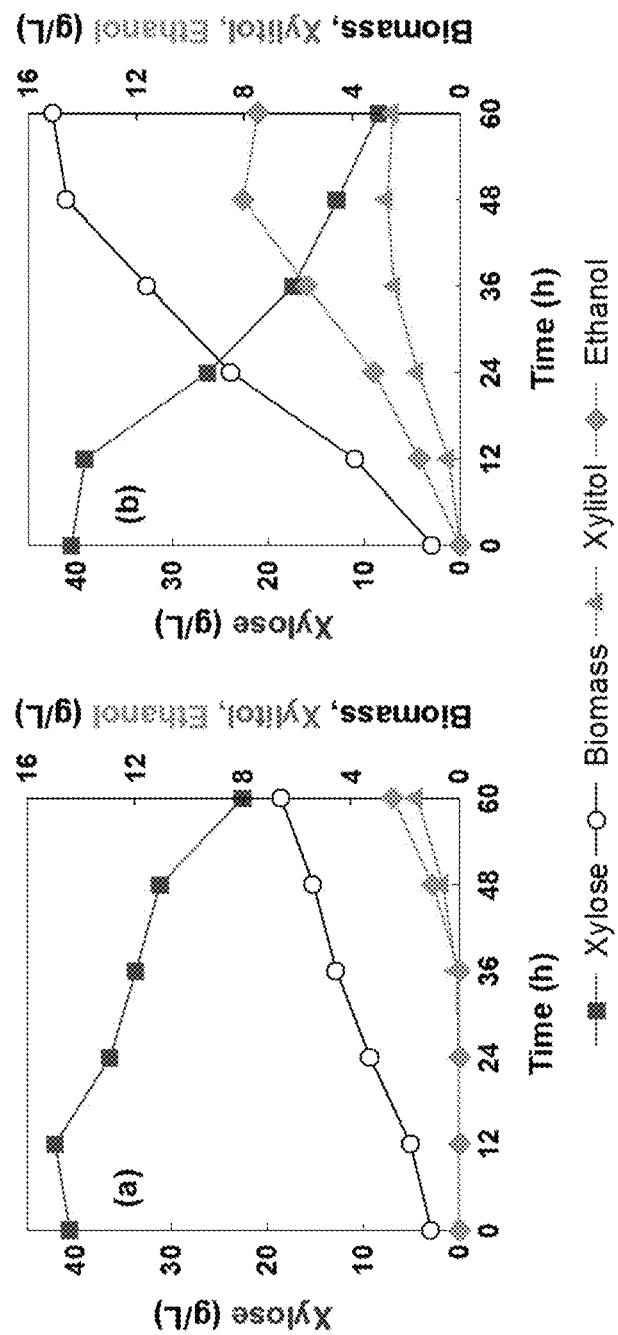
FIG. 6: The profile of xylose fermentation by DX123 (SsXYL1, SsXYL2 and SsXYL3), with and without PHO13 gene deletion (Δpho13). (A) xylose fermentation by DX123; (B) xylose fermentation by DX123 Δpho13.

Experiments were performed to compare the xylose fermentation profile of DGX23 and DX123 strains having wild-type PHO13 expression or having deletion of the PHO13 gene (ΔPHO13). All strains were grown in 5 ml of YP medium (10 g/l of yeast extract and 20 g/l of peptone) containing 20 g/l of D-glucose (YPD) at 30° C. for 24 hours. The grown cultures were centrifuged and resuspended to 50 ml of YP medium containing 40 g/l of D-xylose (YPX). The cultures were then assayed over time for xylose, biomass, ethanol, and xylitol content (FIGS. 5 and 6). FIG. 5 shows the results from the DGX23 strain (panel A is DGX23; panel B is DGX23 ΔPHO13). FIG. 6 shows the results from the DX123 strain (panel A is DX123; panel B is DX123 ΔPHO13).

As shown in FIG. 5, reducing expression of PHO13 in the DGX23 strain significantly improved the xylose fermentation profile of the DGX23 strain. For example, the DGX23 ΔPHO13 strain had a 6.3-fold greater ethanol production after 60 hours fermentation than the DGX23 strain having normal expression of PHO13. After 60 hours fermentation, DGX23 ΔPHO13 also had nearly double the biomass of a DGX23 strain having normal expression of PHO13, and the DGX23 ΔPHO13 strain also had 3.1-fold higher specific ethanol production rate (g ethanol/g cell h) than the DGX23 strain having normal expression of PHO13 (FIG. 5) [specific ethanol production rate is g ethanol produced by 1 g of biomass in an hour].

As shown in FIG. 6, reducing expression of PHO13 in the DX123 strain also improves the xylose fermentation profile of the DX123 strain, but not to the extent that reducing expression of PHO13 improves xylose fermentation of the DGX23 strain.

As shown in FIGS. 5 and 6, surprisingly, DGX23 ΔPHO13 cells ferment xylose significantly faster and produce more ethanol per liter than DX123 ΔPHO13 cells (compare FIGS. 5B and 6B). This result is surprising, for example and without limitation, because in prior studies of cells overexpressing ScGRE3, cells overexpressing ScGRE3 were less efficient at metabolizing xylose than cells overexpressing SsXYL1 (Traff-Bjerre et al, Yeast, 21: 141-150, (2004); Toivari et al, Appl. Environ. Microbiol, 70: 3681-3686, (2004)).

Additionally, reducing expression of PHO13 in DGX23 cells surprisingly improves xylose metabolism by DGX23 cells to a much greater extent than reducing expression of PHO13 in the DX123 strain improves xylose metabolism by DX123 cells. For example, after 60 hours fermentation, the DGX23 ΔPHO13 strain had 6.3-fold greater ethanol yield than the DGX23 strain (compare FIGS. 5B and 5A), whereas after 60 hours fermentation, the DX123 ΔPHO13 strain had only a 3.1-fold greater ethanol yield than the DX123 strain (compare FIGS. 6B and 6A).

All fermentation experiments were started with the initial OD 1 and incubated at 30° C. and at 100 rpm.

What is claimed:

1. A host cell comprising:
   a) a recombinant polynucleotide encoding an aldose reductase comprising an amino acid sequence having at least 90% identity to SEQ ID NO: 2;
   b) a recombinant polynucleotide encoding a xylitol dehydrogenase comprising an amino acid sequence having at least 90% identity to SEQ ID NO: 6; and
   c) a recombinant polynucleotide encoding a xylulokinase comprising an amino acid sequence having at least 90% identity to SEQ ID NO: 8.

2. The host cell of claim 1, wherein
   the recombinant polynucleotide encoding an aldose reductase encodes a polypeptide comprising SEQ ID NO: 2;
   the recombinant polynucleotide encoding a xylitol dehydrogenase encodes a polypeptide comprising SEQ ID NO: 6; and
   the recombinant polynucleotide encoding a xylulokinase encodes a polypeptide comprising SEQ ID NO: 8.

3. The host cell of claim 1, wherein the host cell has a modification affecting the expression of PHO13 or a PHO13 ortholog, and wherein the modification is an insertion, deletion, and/or mutation in the PHO13 or PHO13 ortholog gene.

4. The host cell of claim 1, wherein the host cell is a *Saccharomyces cerevisiae* (*S. cerevisiae*) cell.

5. The host cell of claim 1, wherein one or more of the recombinant polynucleotides are under the control of a constitutive promoter.

6. The host cell of claim 1, wherein all of the recombinant polynucleotides are under the control of a constitutive promoter.

7. The host cell of claim 1, wherein the host cell further comprises one or more recombinant polynucleotides that encode a hemicellulase.

8. The host cell of claim 7, wherein the host cell comprises a recombinant polynucleotide that encodes a xylanase.

9. A method of increasing the consumption of xylose by a cell in xylose-containing material, the method comprising incubating the host cell of claim 1 in xylose-containing material under conditions sufficient to support the expression of said recombinant polynucleotides, wherein the host cell consumes more xylose than a corresponding host cell lacking said recombinant polynucleotides.

10. The method of claim 9, wherein the host cell produces more ethanol than a corresponding host cell lacking said recombinant polynucleotides.

11. The method of claim 9, wherein the xylose-containing material is incubated with the host cell under conditions that support the generation of a fermentation product.

12. The host cell of claim 2, wherein the host cell has a modification affecting the expression of PHO13 or a PHO13 ortholog, and wherein the modification is an insertion, deletion, and/or mutation in the PHO13 or PHO13 ortholog gene.

13. The host cell of claim 2, wherein the host cell is a *Saccharomyces cerevisiae* (*S. cerevisiae*) cell.

14. The host cell of claim 2, wherein one or more of the recombinant polynucleotides are under the control of a constitutive promoter.

15. The host cell of claim 2, wherein all of the recombinant polynucleotides are under the control of a constitutive promoter.

16. The host cell of claim 2, wherein the host cell further comprises one or more recombinant polynucleotides that encode a hemicellulase.

17. The host cell of claim 16, wherein the host cell comprises a recombinant polynucleotide that encodes a xylanase.

* * * * *

SEQUENCE LISTING

<160> NUMBER OF SEQ ID NOS: 12

<210> SEQ ID NO 1
<211> LENGTH: 984
<212> TYPE: DNA
<213> ORGANISM: Saccharomyces cerevisiae

<400> SEQUENCE: 1

```
atgtcttcac tggttactct taataacggt ctgaaaatgc ccctagtcgg cttagggtgc      60
tggaaaattg acaaaaaagt ctgtgcgaat caaatttatg aagctatcaa attaggctac     120
cgtttattcg atggtgcttg cgactacggc aacgaaaagg aagttggtga aggtatcagg     180
aaagccatct ccgaaggtct tgtttctaga aaggatatat ttgttgtttc aaagttatgg     240
aacaattttc accatcctga tcatgtaaaa ttagctttaa agaagacctt aagcgatatg     300
ggacttgatt atttagacct gtattatatt cacttcccaa tcgccttcaa atatgttcca     360
tttgaagaga aatacccctcc aggattctat acgggcgcag atgacgagaa gaaggtcac      420 atcaccgaag cacatgtacc aatcatagat acgtaccggg ctctggaaga atgtgttgat     480
gaaggcttga ttaagtctat tggtgtttcc aactttcagg gaagcttgat tcaagattta     540
ttacgtggtt gtagaatcaa gcccgtggct ttgcaaattg aacaccatcc ttatttgact     600
caagaacacc tagttgagtt ttgtaaatta cacgatatcc aagtagttgc ttactcctcc     660
ttcggtcctc aatcattcat tgagatggac ttacagttgg caaaaaccac gccaactctg     720
ttcgagaatg atgtaatcaa gaaggtctca caaaaccatc caggcagtac cacttcccaa     780
gtattgctta gatgggcaac tcagagaggc attgccgtca ttccaaaatc ttccaagaag     840
gaaaggttac ttggcaacct agaaatcgaa aaaaagttca ctttaacgga gcaagaattg     900
aaggatattt ctgcactaaa tgccaacatc agatttaatg atccatggac ctggttggat     960
ggtaaattcc ccacttttgc ctga                                            984
```

<210> SEQ ID NO 2
<211> LENGTH: 327
<212> TYPE: PRT
<213> ORGANISM: Saccharomyces cerevisiae

<400> SEQUENCE: 2

```
Met Ser Ser Leu Val Thr Leu Asn Asn Gly Leu Lys Met Pro Leu Val
 1               5                  10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
                100                 105                 110

Pro Ile Ala Phe Lys Tyr Val Pro Phe Glu Glu Lys Tyr Pro Pro Gly
            115                 120                 125

Phe Tyr Thr Gly Ala Asp Asp Glu Lys Lys Gly His Ile Thr Glu Ala
        130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 3
<211> LENGTH: 957
<212> TYPE: DNA
<213> ORGANISM: Scheffersomyces stipitis

<400> SEQUENCE: 3
atgccttcta ttaagttgaa ctctggttac gacatgccag ccgtcggttt cggctgttgg     60
aaagtcgacg tcgacaccct gttctgaacag atctaccgtg ctatcaagac cggttacaga    120
ttgttcgacg gtgccgaaga ttacgccaac gaaaagttag ttggtgccgg tgtcaagaag    180
gccattgacg aaggtatcgt caagcgtgaa gacttgttcc ttacctccaa gttgtggaac    240
```

```
aactaccacc acccagacaa cgtcgaaaag gccttgaaca gaaccctttc tgacttgcaa    300
gttgactacg ttgacttgtt cttgatccac ttcccagtca ccttcaagtt cgttccatta    360
gaagaaaagt acccaccagg attctactgt ggtaagggtg acaacttcga ctacgaagat    420
gttccaattt tagagacctg gaaggctctt gaaaagttgg tcaaggccgg taagatcaga    480
tctatcggtg tttctaactt cccaggtgct tgctcttgg acttgttgag aggtgctacc    540
atcaagccat ctgtcttgca agttaacac cacccatact tgcaacaacc aagattgatc    600
gaattcgctc aatcccgtgg tattgctgtc accgcttact cttcgttcgg tcctcaatct    660
ttcgttgaat tgaaccaagg tagagctttg aacacttctc cattgttcga aacgaaact     720
atcaaggcta tcgctgctaa gcacggtaag tctccagctc aagtcttgtt gagatggtct    780
tcccaaagag gcattgccat cattccaaag tccaacactg tcccaagatt gttggaaaac    840
aaggacgtca acagcttcga cttggacgaa caagatttcg ctgacattgc caagttggac    900
atcaacttga gattcaacga cccatgggac tgggacaaga ttcctatctt cgtctaa      957

<210> SEQ ID NO 4
<211> LENGTH: 318
<212> TYPE: PRT
<213> ORGANISM: Scheffersomyces stipitis

<400> SEQUENCE: 4

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255
```

```
Leu Arg Trp Ser Ser Gln Arg Gly Ile Ala Ile Ile Pro Lys Ser Asn
        260                 265                 270

Thr Val Pro Arg Leu Leu Glu Asn Lys Asp Val Asn Ser Phe Asp Leu
    275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 5
<211> LENGTH: 1092
<212> TYPE: DNA
<213> ORGANISM: Scheffersomyces stipitis

<400> SEQUENCE: 5
atgactgcta acccttcctt ggtgttgaac aagatcgacg acatttcgtt cgaaacttac     60
gatgccccag aaatctctga acctaccgat gtcctcgtcc aggtcaagaa aaccggtatc    120
tgtggttccg acatccactt ctacgcccat ggtagaatcg gtaacttcgt tttgaccaag    180
ccaatggtct tgggtcacga atccgccggt actgttgtcc aggttggtaa gggtgtcacc    240
tctcttaagg ttggtgacaa cgtcgctatc gaaccaggta ttccatccag attctccgac    300
gaatacaaga gcggtcacta caacttgtgt cctcacatgg ccttcgccgc tactcctaac    360
tccaaggaag gcgaaccaaa cccaccaggt accttatgta agtacttcaa gtcgccagaa    420
gacttcttgg tcaagttgcc agaccacgtc agcttggaac tcggtgctct tgttgagcca    480
ttgtctgttg gtgtccacgc ctctaagttg ggttccgttg ctttcggcga ctacgttgcc    540
gtctttggtg ctggtcctgt tggtctttg gctgctgctg tcgccaagac cttcggtgct    600
aagggtgtca tcgtcgttga cattttcgac aacaagttga agatggccaa ggacattggt    660
gctgctactc acaccttcaa ctccaagacc ggtggttctg aagaattgat caaggctttc    720
ggtggtaacg tgccaaacgt cgtttggaa tgtactggtg ctgaaccttg tatcaagttg    780
ggtgttgacg ccattgcccc aggtggtcgt ttcgttcaag tcggtaacgc tgctggtcca    840
gtcagcttcc caatcaccgt tttcgccatg aaggaattga ctttgttcgg ttcttttcaga    900 tacggattca cgactacaa gactgctgtt ggaatctttg acactaacta ccaaaacggt    960
agagaaaatg ctccaattga ctttgaacaa ttgatcaccc acagatacaa gttcaaggac   1020
gctattgaag cctacgactt ggtcagagcc ggtaagggtg ctgtcaagtg tctcattgac   1080
ggccctgagt aa                                                        1092

<210> SEQ ID NO 6
<211> LENGTH: 363
<212> TYPE: PRT
<213> ORGANISM: Scheffersomyces stipitis

<400> SEQUENCE: 6

Met Thr Ala Asn Pro Ser Leu Val Leu Asn Lys Ile Asp Asp Ile Ser
 1               5                  10                  15

Phe Glu Thr Tyr Asp Ala Pro Glu Ile Ser Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80
```

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 7
<211> LENGTH: 1872
<212> TYPE: DNA
<213> ORGANISM: Scheffersomyces stipitis

<400> SEQUENCE: 7
atgaccacta cccccatttga tgctccagat aagctcttcc tcggggttcga tctttcgact    60 cagcagttga agatcatcgt caccgatgaa aacctcgctg ctctcaaaac ctacaatgtc   120
gagttcgata gcatcaacag ctctgtccag aagggtgtca ttgctatcaa cgacgaaatc   180
agcaagggtg ccattatttc ccccgtttac atgtggttgg atgcccttga ccatgttttt   240
gaagacatga agaaggacgg attcccttc  aacaaggttg ttggtatttc cggttcttgt   300
caacagcacg gttcggtata ctggtctaga acggccgaga aggtcttgtc gaattggac   360 gctgaatctt cgttatcgag ccagatgaga tctgctttca ccttcaagca cgctccaaac   420
tggcaggatc actctaccgg taaagagctt gaagagttcg aaagagtgat tggtgctgat   480
gccttggctg atatctctgg ttccagagcc cattacagat tcacagggct ccagattaga   540

```
aagttgtcta ccagattcaa gcccgaaaag tacaacagaa ctgctcgtat ctctttagtt    600
tcgtcatttg ttgccagtgt gttgcttggt agaatcacct ccattgaaga ggccgatgct    660
tgtggaatga acttgtacga tatcgaaaag cgcgagttca cgaagagct cttggccatc    720 gctgctggtg tccaccctga gttggatggt gtagaacaag acggtgaaat ttacagagct    780
ggtatcaatg agttgaagag aaagttgggt cctgtcaaac ctataacata cgaaagcgaa    840
ggtgacattg cctcttactt tgtcaccaga tacggcttca accccgactg taaaatctac    900
tcgttcaccg gagacaattt ggccacgatt atctcgttgc ctttggctcc aaatgatgct    960
ttgatctcat tgggtacttc tactacagtt ttaattatca ccaagaacta cgctccttct   1020
tctcaatacc atttgtttaa acatccaacc atgcctgacc actacatggg catgatctgc   1080
tactgtaacg gttccttggc cagagaaaag gttagagacg aagtcaacga aagttcaat    1140 gtagaagaca agaagtcgtg ggacaagttc aatgaaatct tggacaaatc cacagacttc   1200
aacaacaagt tgggtattta cttcccactt ggcgaaattg tccctaatgc cgctgctcag   1260
atcaagagat cggtgttgaa cagcaagaac gaaattgtag acgttgagtt gggcgacaag   1320
aactggcaac tgaagatgat gtttcttca attgtagaat cacagacttt gtcttgtaga   1380
ttgagaactg gtccaatgtt gagcaagagt ggagattctt ctgcttccag ctctgcctca   1440
cctcaaccag aaggtgatgg tacagatttg cacaaggtct accagacttt ggttaaaaag   1500
tttggtgact tgtacactga tggaagaag caaaccttg agtctttgac cgccagacct   1560
aaccgttgtt actacgtcgg tggtgcttcc aacaacggca gcattatccg caagatgggt   1620
tccatcttgg ctcccgtcaa cggaaactac aaggttgaca ttcctaacgc ctgtgcattg   1680
ggtggtgctt acaaggccag ttggagttac gagtgtgaag ccaagaagga atggatcgga   1740
tacgatcagt atatcaacag attgtttgaa gtaagtgacg agatgaatct gttcgaagtc   1800
aaggataaat ggctcgaata tgccaacggg gttggaatgt tggccaagat ggaaagtgaa   1860
ttgaaacact aa                                                       1872

<210> SEQ ID NO 8
<211> LENGTH: 623
<212> TYPE: PRT
<213> ORGANISM: Scheffersomyces stipitis

<400> SEQUENCE: 8
```

Met Thr Thr Thr Pro Phe Asp Ala Pro Asp Lys Leu Phe Leu Gly Phe
1               5                   10                  15

Asp Leu Ser Thr Gln Gln Leu Lys Ile Ile Val Thr Asp Glu Asn Leu
            20                  25                  30

Ala Ala Leu Lys Thr Tyr Asn Val Glu Phe Asp Ser Ile Asn Ser Ser
        35                  40                  45

Val Gln Lys Gly Val Ile Ala Ile Asn Asp Glu Ile Ser Lys Gly Ala
    50                  55                  60

Ile Ile Ser Pro Val Tyr Met Trp Leu Asp Ala Leu Asp His Val Phe
65                  70                  75                  80

Glu Asp Met Lys Lys Asp Gly Phe Pro Phe Asn Lys Val Val Gly Ile
                85                  90                  95

Ser Gly Ser Cys Gln Gln His Gly Ser Val Tyr Trp Ser Arg Thr Ala
            100                 105                 110

Glu Lys Val Leu Ser Glu Leu Asp Ala Glu Ser Ser Leu Ser Ser Gln
        115                 120                 125

Met Arg Ser Ala Phe Thr Phe Lys His Ala Pro Asn Trp Gln Asp His

```
            130                 135                 140
Ser Thr Gly Lys Glu Leu Glu Glu Phe Glu Arg Val Ile Gly Ala Asp
145                 150                 155                 160

Ala Leu Ala Asp Ile Ser Gly Ser Arg Ala His Tyr Arg Phe Thr Gly
                165                 170                 175

Leu Gln Ile Arg Lys Leu Ser Thr Arg Phe Lys Pro Glu Lys Tyr Asn
                180                 185                 190

Arg Thr Ala Arg Ile Ser Leu Val Ser Ser Phe Val Ala Ser Val Leu
                195                 200                 205

Leu Gly Arg Ile Thr Ser Ile Glu Glu Ala Asp Ala Cys Gly Met Asn
210                 215                 220

Leu Tyr Asp Ile Glu Lys Arg Glu Phe Asn Glu Leu Leu Ala Ile
225                 230                 235                 240

Ala Ala Gly Val His Pro Glu Leu Asp Gly Val Glu Gln Asp Gly Glu
                245                 250                 255

Ile Tyr Arg Ala Gly Ile Asn Glu Leu Lys Arg Lys Leu Gly Pro Val
                260                 265                 270

Lys Pro Ile Thr Tyr Glu Ser Glu Gly Asp Ile Ala Ser Tyr Phe Val
                275                 280                 285

Thr Arg Tyr Gly Phe Asn Pro Asp Cys Lys Ile Tyr Ser Phe Thr Gly
                290                 295                 300

Asp Asn Leu Ala Thr Ile Ile Ser Leu Pro Leu Ala Pro Asn Asp Ala
305                 310                 315                 320

Leu Ile Ser Leu Gly Thr Ser Thr Thr Val Leu Ile Ile Thr Lys Asn
                325                 330                 335

Tyr Ala Pro Ser Ser Gln Tyr His Leu Phe Lys His Pro Thr Met Pro
                340                 345                 350

Asp His Tyr Met Gly Met Ile Cys Tyr Cys Asn Gly Ser Leu Ala Arg
                355                 360                 365

Glu Lys Val Arg Asp Glu Val Asn Glu Lys Phe Asn Val Glu Asp Lys
                370                 375                 380

Lys Ser Trp Asp Lys Phe Asn Glu Ile Leu Asp Lys Ser Thr Asp Phe
385                 390                 395                 400

Asn Asn Lys Leu Gly Ile Tyr Phe Pro Leu Gly Glu Ile Val Pro Asn
                405                 410                 415

Ala Ala Ala Gln Ile Lys Arg Ser Val Leu Asn Ser Lys Asn Glu Ile
                420                 425                 430

Val Asp Val Glu Leu Gly Asp Lys Asn Trp Gln Pro Glu Asp Asp Val
                435                 440                 445

Ser Ser Ile Val Glu Ser Gln Thr Leu Ser Cys Arg Leu Arg Thr Gly
                450                 455                 460

Pro Met Leu Ser Lys Ser Gly Asp Ser Ser Ala Ser Ser Ser Ala Ser
465                 470                 475                 480

Pro Gln Pro Glu Gly Asp Gly Thr Asp Leu His Lys Val Tyr Gln Asp
                485                 490                 495

Leu Val Lys Lys Phe Gly Asp Leu Tyr Thr Asp Gly Lys Lys Gln Thr
                500                 505                 510

Phe Glu Ser Leu Thr Ala Arg Pro Asn Arg Cys Tyr Tyr Val Gly Gly
                515                 520                 525

Ala Ser Asn Asn Gly Ser Ile Ile Arg Lys Met Gly Ser Ile Leu Ala
                530                 535                 540

Pro Val Asn Gly Asn Tyr Lys Val Asp Ile Pro Asn Ala Cys Ala Leu
545                 550                 555                 560
```

```
Gly Gly Ala Tyr Lys Ala Ser Trp Ser Tyr Glu Cys Glu Ala Lys Lys
            565                 570                 575

Glu Trp Ile Gly Tyr Asp Gln Tyr Ile Asn Arg Leu Phe Glu Val Ser
        580                 585                 590

Asp Glu Met Asn Leu Phe Glu Val Lys Asp Lys Trp Leu Glu Tyr Ala
        595                 600                 605

Asn Gly Val Gly Met Leu Ala Lys Met Glu Ser Glu Leu Lys His
    610                 615                 620

<210> SEQ ID NO 9
<211> LENGTH: 1803
<212> TYPE: DNA
<213> ORGANISM: Saccharomyces cerevisiae

<400> SEQUENCE: 9
atgttgtgtt cagtaattca gagacagaca agagaggttt ccaacacaat gtctttagac      60
tcatactatc ttgggtttga tctttcgacc caacaactga aatgtctcgc cattaaccag     120
gacctaaaaa ttgtccattc agaaacagtg gaatttgaaa aggatcttcc gcattatcac     180
acaaagaagg gtgtctatat acacggcgac actatcgaat gtcccgtagc catgtggtta     240
gaggctctag atctggttct ctcgaaatat cgcgaggcta aatttccatt gaacaaagtt     300
atggccgtct cagggtcctg ccagcagcac gggtctgtct actggtcctc ccaagccgaa     360
tctctgttag agcaattgaa taagaaaccg gaaaagatt tattgcacta cgtgagctct     420
gtagcatttg caaggcaaac cgcccccaat tggcaagacc acagtactgc aaagcaatgt     480
caagagtttg aagagtgcat aggtgggcct gaaaaaatgg ctcaattaac agggtccaga     540
gcccatttta gatttactgg tcctcaaatt ctgaaaattg cacaattaga accagaagct     600
tacgaaaaaa caaagaccat ttctttagtg tctaattttt tgacttctat cttagtgggc     660
catcttgttg aattagagga ggcagatgcc tgtggtatga ccttttatga tatacgtgaa     720
agaaaattca gtgatgagct actacatcta attgatagtt cttctaagga taaaactatc     780
agacaaaaat taatgagagc acccatgaaa aatttgatag cgggtaccat ctgtaaatat     840
tttattgaga agtacggttt caatacaaac tgcaaggtct ctcccatgac tggggataat     900
ttagccacta tatgttcttt accccctgcg gaagaatgacg ttctcgtttc cctaggaaca     960
agtactacag ttcttctggt caccgataag tatcaccctt ctccgaacta tcatctttc    1020 attcatccaa ctctgccaaa ccattatatg ggtatgattt gttattgtaa tggttctttg   1080
gcaagggaga ggataagaga cgagttaaac aaagaacggg aaaataatta tgagaagact   1140
aacgattgga ctcttttttaa tcaagctgtg ctagatgact cagaaagtag tgaaaatgaa   1200
ttaggtgtat attttcctct ggggggagatc gttcctagcg taaagccat aaacaaaagg   1260 gttatcttca atccaaaaac gggtatgatt gaaagagagg tggccaagtt caaagacaag   1320
aggcacgatg ccaaaaatat tgtagaatca caggctttaa gttgcagggt aagaatatct   1380
cccctgcttt cggattcaaa cgcaagctca acagagac tgaacgaaga tacaatcgtg   1440
aagtttgatt acgatgaatc tccgctgcgg gactacctaa ataaaggcc agaaaggact   1500 ttttttgtag gtggggcttc taaaaacgat gctattgtga agaagtttgc tcaagtcatt   1560
ggtgctacaa agggtaattt taggctgaaa acaccaaact catgtgccct tggtggttgt   1620
tataaggcca tgtggtcatt gttatatgac tctaataaaa ttgcagttcc ttttgataaa   1680
tttctgaatg acaattttcc atggcatgta atggaaagca tatccgatgt ggataatgaa   1740
aattgggatc gctataattc caagattgtc cccttaagcg aactgaaaaa gactctcatc   1800
```

```
taa                                                              1803
```

<210> SEQ ID NO 10
<211> LENGTH: 600
<212> TYPE: PRT
<213> ORGANISM: Saccharomyces cerevisiae

<400> SEQUENCE: 10

```
Met Leu Cys Ser Val Ile Gln Arg Gln Thr Arg Glu Val Ser Asn Thr
  1               5                  10                  15

Met Ser Leu Asp Ser Tyr Tyr Leu Gly Phe Asp Leu Ser Thr Gln Gln
             20                  25                  30

Leu Lys Cys Leu Ala Ile Asn Gln Asp Leu Lys Ile Val His Ser Glu
         35                  40                  45

Thr Val Glu Phe Glu Lys Asp Leu Pro His Tyr His Thr Lys Lys Gly
     50                  55                  60

Val Tyr Ile His Gly Asp Thr Ile Glu Cys Pro Val Ala Met Trp Leu
 65                  70                  75                  80

Glu Ala Leu Asp Leu Val Leu Ser Lys Tyr Arg Glu Ala Lys Phe Pro
                 85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
```

```
                370             375             380
Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
                420                 425                 430

Glu Val Ala Lys Phe Lys Asp Lys Arg His Asp Ala Lys Asn Ile Val
                435                 440                 445

Glu Ser Gln Ala Leu Ser Cys Arg Val Arg Ile Ser Pro Leu Leu Ser
450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
                500                 505                 510

Val Lys Lys Phe Ala Gln Val Ile Gly Ala Thr Lys Gly Asn Phe Arg
                515                 520                 525

Leu Glu Thr Pro Asn Ser Cys Ala Leu Gly Gly Cys Tyr Lys Ala Met
530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
                580                 585                 590

Ser Glu Leu Glu Lys Thr Leu Ile
595                 600
```

```
<210> SEQ ID NO 11
<211> LENGTH: 939
<212> TYPE: DNA
<213> ORGANISM: Saccharomyces cerevisiae

<400> SEQUENCE: 11
atgactgctc aacaaggtgt accaataaag ataaccaata aggagattgc tcaagaattc      60
ttggacaaat atgacacgtt tctgttcgat tgtgatggtg tattatggtt aggttctcaa     120
gcattaccat acaccctgga aattctaaac cttttgaagc aattgggcaa caactgatc      180 ttcgttacga ataactctac caagtcccgt ttagcataca cgaaaaagtt tgcttcgttt     240
ggtattgatg tcaaagaaga acagattttc acctctggtt atgcgtcagc tgtttatatt     300
cgtgactttc tgaaattgca gcctggcaaa gataaggtat gggtatttgg agaaagcggt     360
attggtgaag aattgaaact aatggggtac gaatctctag gaggtgccga ttccagattg     420
gatacgccgt tcgatgcagc taaatcacca ttttggtga acggccttga taggatgtt      480 agttgtgtta ttgctgggtt agacacgaag gtaaattacc accgtttggc tgttacactg     540
cagtatttgc agaaggattc tgttcacttt gttggtacaa atgttgattc tactttcccg     600
caaaagggtt atacatttcc cggtgcaggc tccatgattg aatcattggc attctcatct     660
aataggaggc catcgtactg tggtaagcca aatcaaaata tgctaaacag cattatatcg     720
gcattcaacc tggatagatc aaagtgctgt atggttggtg acagattaaa caccgatatg     780
aaattcggtg ttgaaggtgg gttaggtgca cactactcg ttttgagtgg tattgaaacc     840
```

-continued

```
gaagagagag ccttgaagat ttcgcacgat tatccaagac ctaaattta cattgataaa    900 cttggtgaca tctacacctt aaccaataat gagttatag                           939
```

```
<210> SEQ ID NO 12
<211> LENGTH: 312
<212> TYPE: PRT
<213> ORGANISM: Saccharomyces cerevisiae

<400> SEQUENCE: 12
```

| | | | | | | | | | | | | | | | |
|---|---|---|---|---|---|---|---|---|---|---|---|---|---|---|---|
| Met | Thr | Ala | Gln | Gln | Gly | Val | Pro | Ile | Lys | Ile | Thr | Asn | Lys | Glu | Ile |
| 1 | | | | 5 | | | | | 10 | | | | | 15 | |
| Ala | Gln | Glu | Phe | Leu | Asp | Lys | Tyr | Asp | Thr | Phe | Leu | Phe | Asp | Cys | Asp |
| | | | 20 | | | | | 25 | | | | | 30 | | |
| Gly | Val | Leu | Trp | Leu | Gly | Ser | Gln | Ala | Leu | Pro | Tyr | Thr | Leu | Glu | Ile |
| | | | 35 | | | | | 40 | | | | | 45 | | |
| Leu | Asn | Leu | Leu | Lys | Gln | Leu | Gly | Lys | Gln | Leu | Ile | Phe | Val | Thr | Asn |
| | | 50 | | | | | 55 | | | | | 60 | | | |
| Asn | Ser | Thr | Lys | Ser | Arg | Leu | Ala | Tyr | Thr | Lys | Lys | Phe | Ala | Ser | Phe |
| 65 | | | | | 70 | | | | | 75 | | | | | 80 |
| Gly | Ile | Asp | Val | Lys | Glu | Glu | Gln | Ile | Phe | Thr | Ser | Gly | Tyr | Ala | Ser |
| | | | | 85 | | | | | 90 | | | | | 95 | |
| Ala | Val | Tyr | Ile | Arg | Asp | Phe | Leu | Lys | Leu | Gln | Pro | Gly | Lys | Asp | Lys |
| | | | 100 | | | | | 105 | | | | | 110 | | |
| Val | Trp | Val | Phe | Gly | Glu | Ser | Gly | Ile | Gly | Glu | Glu | Leu | Lys | Leu | Met |
| | | | 115 | | | | | 120 | | | | | 125 | | |
| Gly | Tyr | Glu | Ser | Leu | Gly | Gly | Ala | Asp | Ser | Arg | Leu | Asp | Thr | Pro | Phe |
| | | 130 | | | | | 135 | | | | | 140 | | | |
| Asp | Ala | Ala | Lys | Ser | Pro | Phe | Leu | Val | Asn | Gly | Leu | Asp | Lys | Asp | Val |
| 145 | | | | | 150 | | | | | 155 | | | | | 160 |
| Ser | Cys | Val | Ile | Ala | Gly | Leu | Asp | Thr | Lys | Val | Asn | Tyr | His | Arg | Leu |
| | | | | 165 | | | | | 170 | | | | | 175 | |
| Ala | Val | Thr | Leu | Gln | Tyr | Leu | Gln | Lys | Asp | Ser | Val | His | Phe | Val | Gly |
| | | | 180 | | | | | 185 | | | | | 190 | | |
| Thr | Asn | Val | Asp | Ser | Thr | Phe | Pro | Gln | Lys | Gly | Tyr | Thr | Phe | Pro | Gly |
| | | | 195 | | | | | 200 | | | | | 205 | | |
| Ala | Gly | Ser | Met | Ile | Glu | Ser | Leu | Ala | Phe | Ser | Ser | Asn | Arg | Arg | Pro |
| | | 210 | | | | | 215 | | | | | 220 | | | |
| Ser | Tyr | Cys | Gly | Lys | Pro | Asn | Gln | Asn | Met | Leu | Asn | Ser | Ile | Ile | Ser |
| 225 | | | | | 230 | | | | | 235 | | | | | 240 |
| Ala | Phe | Asn | Leu | Asp | Arg | Ser | Lys | Cys | Cys | Met | Val | Gly | Asp | Arg | Leu |
| | | | | 245 | | | | | 250 | | | | | 255 | |
| Asn | Thr | Asp | Met | Lys | Phe | Gly | Val | Glu | Gly | Gly | Leu | Gly | Gly | Thr | Leu |
| | | | 260 | | | | | 265 | | | | | 270 | | |
| Leu | Val | Leu | Ser | Gly | Ile | Glu | Thr | Glu | Glu | Arg | Ala | Leu | Lys | Ile | Ser |
| | | | 275 | | | | | 280 | | | | | 285 | | |
| His | Asp | Tyr | Pro | Arg | Pro | Lys | Phe | Tyr | Ile | Asp | Lys | Leu | Gly | Asp | Ile |
| | | 290 | | | | | 295 | | | | | 300 | | | |
| Tyr | Thr | Leu | Thr | Asn | Asn | Glu | Leu | | | | | | | | |
| 305 | | | | | 310 | | | | | | | | | | |